United States Patent
Wang et al.

(10) Patent No.: US 9,373,801 B2
(45) Date of Patent: Jun. 21, 2016

(54) FLAVANTHRENE DERIVATIVES AND THEIR USE AS ORGANIC SEMICONDUCTORS

(75) Inventors: Changsheng Wang, Durham (GB); William Mitchell, Chandler's Ford (GB); Mansoor D'Lavari, Bude (GB); Steven Tierney, Southampton (GB)

(73) Assignee: MERCK PATENT GMBH, Darmstadt (DE)

(*) Notice: Subject to any disclaimer, the term of this patent is extended or adjusted under 35 U.S.C. 154(b) by 195 days.

(21) Appl. No.: 13/982,004

(22) PCT Filed: Jan. 4, 2012

(86) PCT No.: PCT/EP2012/000022
§ 371 (c)(1),
(2), (4) Date: Jul. 26, 2013

(87) PCT Pub. No.: WO2012/100900
PCT Pub. Date: Aug. 2, 2012

(65) Prior Publication Data
US 2013/0306914 A1 Nov. 21, 2013

(30) Foreign Application Priority Data
Jan. 28, 2011 (EP) .................................. 11000696

(51) Int. Cl.
*H01L 51/00* (2006.01)
*C07F 7/08* (2006.01)
*H01L 51/05* (2006.01)

(52) U.S. Cl.
CPC .......... *H01L 51/0094* (2013.01); *C07F 7/0812* (2013.01); *H01L 51/0072* (2013.01); *H01L 51/0541* (2013.01); *H01L 51/0558* (2013.01); *Y02E 10/549* (2013.01)

(58) Field of Classification Search
CPC . H01L 51/0094; H01L 51/00; H01L 51/0072; H01L 51/0077; C07F 7/08; C07F 7/0812; C07F 7/30
USPC ..................... 252/500, 519.2, 519.31; 546/14
See application file for complete search history.

(56) References Cited

U.S. PATENT DOCUMENTS

2011/0073813 A1 3/2011 Caldwell et al.
2012/0048377 A1 3/2012 Winzenberg et al.

FOREIGN PATENT DOCUMENTS

| WO | WO 02057377 A1 * | 7/2002 |
| WO | 2009/155106 A1 | 12/2009 |
| WO | 2010/099583 A1 | 9/2010 |

OTHER PUBLICATIONS

Chinese Office Action dated Dec. 22, 2014 issued in corresponding 201280006540.X application (pp. 1-7).
J. Aoki, "Reduction Product and Leuco-form of Flavanthrone", Bulletin of the Chemical Society of Japan, vol. 41 (1968) pp. 1017-1020.
International Search Report for PCT/EP2012/000022 (May 2, 2012).
Y.Y. Liu et al., "High and Balanced Hole and Electron Mobilities from Ambipolar Thin-Film Transistors Based on Nitrogen-Containing Oligoacenes", Journal of the American Chemical Society, vol. 132, No. 46 (Nov. 2010) pp. 16349-16351.
S. Miao et al., "6,13-Diethynyl-5,7,12,14-tetraazapentacene", Chemistry, A European Journal, vol. 15, No. 20 (May 2009) pp. 4990-4993.

* cited by examiner

*Primary Examiner* — Douglas McGinty
(74) *Attorney, Agent, or Firm* — Miller, White, Zelano, Branigan, P.C.

(57) ABSTRACT

The invention relates to benzo[h]benz[5,6]acridino[2,1,9,8-klmna]acridines, methods of their preparation, their use as semiconductors in organic electronic (OE) devices, and to OE devices comprising them.

11 Claims, No Drawings

FLAVANTHRENE DERIVATIVES AND THEIR USE AS ORGANIC SEMICONDUCTORS

FIELD OF THE INVENTION

The invention relates to benzo[h]benz[5,6]acridino[2,1,9,8-klmna]acridines, methods of their preparation, their use as semiconductors in organic electronic (OE) devices, and OE devices comprising them.

BACKGROUND AND PRIOR ART

Organic semiconductors (OSCs) are expected to revolutionise the manufacturing process of the thin film field-effect transistors (TFTs) used for display technologies. Compared with the classical Si based field-effect transistor (FETs), organic TFTs can be fabricated much more cost-effectively by solution coating methods such as spin-coating, drop casting, dip-coating, and more efficiently, ink-jet printing. Solution processing of OSCs requires the molecular materials to be 1) soluble enough in non-toxic solvents; 2) stable in the solution state; 3) easy to crystallise when solvents are evaporated; and most importantly, 4) to provide high charge carrier mobilities with low off currents. In this context, pentacenes and hetero-acenes with solublising substituents, have shown to be promising classes of p-type OSC materials. Notably, unsymmetrically substituted pentacenes have shown hole mobility greater than 3 $cm^2/Vs$, as disclosed in WO 2009/155106 A1 while fluorinated anthracenodithiophene derivatives (F-ADTs) have shown hole mobility greater than 1 $cm^2/Vs$, as disclosed in US 2008/0128680 A1 and Payne et al., *J. Am. Chem. Soc.*, 2005, 127 (14), 4986; and Subramanian et al., *J. Am. Chem. Soc.* 2008, 130(9), 2706-2707.

However, some major drawbacks remain for these materials, which include low photo and environment stability, particularly in solution states, and a low temperature of phase transition and melting point. Also for future OLED backplane applications, which demand higher source and drain current, the mobility and processibility of currently available materials needs further improvement.

Acenes larger than pentacene keep attracting interests in the quest for novel OSCs due to the predicted lower reorganization energy (see Deng et al., *J. Phys. Chem. B*, 2004, 108, 8614) and the potential higher charge carrier mobility (see Cheng et al., *J. Chem. Phys.*, 2003, 118, 3764). However, linear elongation of the aromatic cores by fusing additional benzene rings is witnessed by the decreased stability and solubility in organic solvents, which compromised the practical application of these analogues as OSC materials (see Purushothaman et al., *Org. Lett.*, 2010, 12(9), 2060). Interestingly, polycyclic aromatic hydrocarbons much larger than pentacene have either been synthesized as nano materials (see Yang et al., *J. Am. Chem. Soc.*, 2008, 130 (13), 4216) or existed in nature as dye stuffs without stability issues due to their 2-D fusing features. This type of structure is most notably represented by free-standing graphene, a class of intrinsic 2-D polycyclic aromatic system, of which large charge carries mobilities exceeding $10^4$ $cm^2/Vs$ have been observed under ambient conditions (see Geim et al., *Nat. Mater.*, 2007, 6(3), 183-191; and Allen et al., *Chem. Rev.*, 2010, 110(1), 132-145), and exceeding $2\times10^5$ $cm^2/Vs$ have been achieved under optimised conditions (see Bolotin et al., *Solid State Commun.*, 2008, 146, 351).

Therefore, there is still a great need for new OSC materials that show good electronic properties, especially high charge carrier mobility, good processibilty and high thermal and environmental stability, and especially a high solubility in organic solvents.

It was an aim of the present invention to provide compounds for use as organic semiconducting materials that do not have the drawbacks of prior art materials as described above, and do especially show good electronic properties, especially high charge carrier mobility, good processibilty and high thermal and environmental stability, and especially a high solubility in organic solvents. Another aim of the invention was to extend the pool of organic semiconducting materials available to the expert.

It was found that these aims can be achieved by providing compounds as claimed in the present invention. These compounds are based on flavanthrone, a industrially available dye stuff with a fused polycyclic aromatic ring structure as shown below, as the starting material.

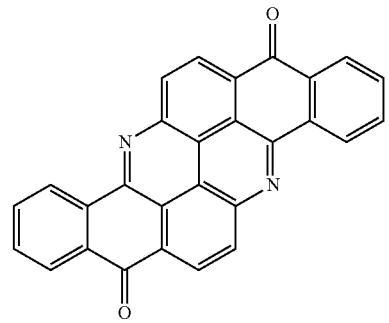 [SMILES: O=c1c2ccccc2c2nc3ccc4c(=O)c5ccccc5c5nc6ccc1c2c6c3c45]

For the purposes of the present invention flavanthrone has been made soluble in organic solvents, so that it becomes solution processible, by the introduction of solublising functional groups through aromatisation of its quinoid structure into a new core unit, i.e. benzo[h]benz[5,6]acridino[2,1,9,8-klmna]acridine (hereinafter also shortly referred to as "flavanthrene"). The inventors of the present invention have found that these flavanthrene derivatives exhibit high solubility in organic solvents, especially those that are typically used in organic electronic device manufacture, and in addition show good thermal stability and high charge carrier mobilities.

No examples of flavanthrene based materials have been reported up to date in the literature.

SUMMARY OF THE INVENTION

The invention relates to compounds of formula I

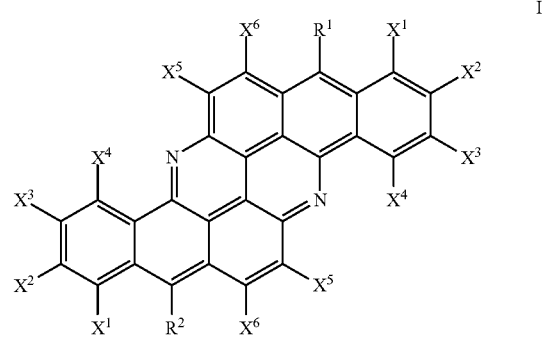

wherein the individual groups have the following meanings
R$^1$ and R$^2$ independently of each other denote straight chain, branched or cyclic alkyl with 1 to 40 C-atoms, which is unsubstituted or substituted by one or more groups L, and wherein one or more non-adjacent CH$_2$ groups are optionally replaced, in each case independently from one another, by —O—, —S—, —NR$^0$—, —SiR$^0$R$^{00}$—, —CY$^0$=CY$^{00}$— or —C≡C— in such a manner that O and/or S atoms are not linked directly to one another, or denote aryl or heteroaryl with 4 to 20 ring atoms which is unsubstituted or substituted by one or more groups L, X$^1$ to X$^6$ independently of each other, and on each occurrence identically or differently, denote H or have one of the meanings given for L, L is selected from P-Sp-, F, Cl, Br, I, —OH, —CN, —NO$_2$, —NCO, —NCS, —OCN, —SCN, —C(=O)NR$^0$R$^{00}$, —C(=O)X$^0$, —C(=O)R$^0$, —NR$^0$R$^{00}$, C(=O)OH, optionally substituted silyl or germyl, optionally substituted aryl or heteroaryl having 4 to 20 ring atoms, straight chain, branched or cyclic alkyl, which is optionally substituted, alkoxy, oxaalkyl or thioalkyl with 1 to 30, preferably 1 to 12 C atoms, each of which is unsubstituted or substituted with one or more F or Cl atoms or OH groups, and straight chain, branched or cyclic alkenyl, alkynyl, alkylcarbonyl, alkoxycarbonyl, alkylcarbonyloxy or alkoxycarbonyloxy with 2 to 20, preferably 2 to 12 C atoms which is unsubstituted or substituted with one or more F or Cl atoms or OH groups, P is a polymerisable group, Sp is a spacer group or a single bond, X$^0$ is halogen, R$^0$ and R$^{00}$ independently of each other denote H or alkyl with 1 to 20 C-atoms, Y$^0$ and Y$^{00}$ independently of each other denote H, F, Cl or CN.

The invention further relates to a formulation comprising one or more compounds of formula I and one or more solvents, preferably selected from organic solvents.

The invention further relates to an organic semiconducting formulation comprising one or more compounds of formula I, one or more organic binders, or precursors thereof, preferably having a permittivity ∈ at 1,000 Hz and 20° C. of 3.3 or less, and optionally one or more solvents.

The invention further relates to the use of compounds and formulations according to the present invention as charge transport, semiconducting, electrically conducting, photoconducting or light emitting material in an optical, electrooptical, electronic, electroluminescent or photoluminescent component or device.

The invention further relates to a charge transport, semiconducting, electrically conducting, photoconducting or light emitting material or component comprising one or more compounds or formulations according to the present invention.

The invention further relates to an optical, electrooptical or electronic component or device comprising one or more compounds, formulations, components or materials according to the present invention.

The optical, electrooptical, electronic, electroluminescent and photoluminescent components or devices include, without limitation, organic field effect transistors (OFET), thin film transistors (TFT), integrated circuits (IC), logic circuits, capacitors, radio frequency identification (RFID) tags, devices or components, organic light emitting diodes (OLED), organic light emitting transistors (OLET), flat panel displays, backlights of displays, organic photovoltaic devices (OPV), solar cells, laser diodes, photoconductors, photodetectors, electrophotographic devices, electrophotographic recording devices, organic memory devices, sensor devices, charge injection layers, charge transport layers or interlayers in polymer light emitting diodes (PLEDs), organic plasmon-emitting diodes (OPEDs), Schottky diodes, planarising layers, antistatic films, polymer electrolyte membranes (PEM), conducting substrates, conducting patterns, electrode materials in batteries, alignment layers, biosensors, biochips, security markings, security devices, and components or devices for detecting and discriminating DNA sequences.

DETAILED DESCRIPTION OF THE INVENTION

This invention relates to a new class of compounds expressed by the general structure as shown in formula I. Apart from being novel, these compounds demonstrate one or more of the following properties:

i) They show good semiconducting properties, especially high charge carrier mobilities and low off-current values in field-effect transistors.

ii) They exhibit excellent photo and thermal stabilities in both solid and solution states.

iii) They have good solubility in non-toxic organic solvents, which allows them to be solution processible.

The compounds of the present invention are easy to synthesize and exhibit several advantageous properties, like a high charge carrier mobility, a high melting point, a high solubility in organic solvents, a good processability for the device manufacture process, a high oxidative and photostability and a long lifetime in electronic devices. In addition, they show advantageous properties as discussed above and below.

In the compounds of formula I R$^1$ and R$^2$ are preferably identical groups.

Very preferred are compounds of formula I wherein R$^1$ and R$^2$ denote —C≡C—R$^3$, wherein R$^3$ is an optionally substituted silyl or germyl group, or an optionally substituted alkyl group or an aryl or heteroaryl group with 4 to 20 ring atoms which is unsubstituted or substituted by one or more groups L as defined above.

If R$^3$ or L is an optionally substituted alkyl, silyl or germyl group, it is preferably selected of the formula II

  II wherein

A is C, Si or Ge, preferably Si, and

R', R", R''' are identical or different groups selected from the group consisting of H, a straight-chain, branched or cyclic alkyl or alkoxy group having 1 to 20 C atoms, a straight-chain, branched or cyclic alkenyl group having 2 to 20 C atoms, a straight-chain, branched or cyclic alkynyl group having 2 to 20 C atoms, a straight-chain, branched or cyclic alkylcarbonyl group having 2 to 20 C atoms, an aryl or heteroaryl group having 4 to 20 ring atoms, an arylalkyl or heteroarylalkyl group having 4 to 20 ring atoms, an aryloxy or heteroaryloxy group having 4 to 20 ring atoms, or an arylalkyloxy or heteroarylalkyloxy group having 4 to 20 ring atoms, wherein all the aforementioned groups are optionally substituted with one or more groups L', and L' has one of the meanings given for L in formula I, which is different from a silyl and germyl group.

Preferably in the compounds of formula I R$^1$ and R$^2$ denote —C≡C—R$^3$, wherein both groups R$^3$ denote identical groups ARR'R" of formula II.

A in formula II is preferably Si.

Preferably, R', R" and R''' in the groups of formula II are each independently selected from optionally substituted and straight-chain, branched or cyclic alkyl or alkoxy having 1 to 10 C atoms, which is for example methyl, ethyl, n-propyl, isopropyl, cyclopropyl, 2,3-dimethyl-cyclopropyl, 2,2,3,3-tetramethylcyclopropyl, tert-butyl, cyclobutyl, cyclo-pentyl, methoxy or ethoxy, optionally substituted and straight-chain, branched or cyclic alkenyl, alkynyl or alkylcarbonyl having 2 to 12 C atoms, which is for example allyl, isopropenyl, 2-but-1-enyl, cis-2-but-2-enyl, 3-but-1-enyl, propynyl or acetyl, optionally substituted aryl, heteroaryl, arylalkyl or heteroarylalkyl, aryloxy or heteroaryloxy having 5 to 10 ring atoms, which is for example phenyl, p-tolyl, benzyl, 2-furanyl, 2-thienyl, 2-selenophenyl, N-methylpyrrol-2-yl or phenoxy.

Further preferred is a group AR'R"R'" of formula II wherein one or more of R', R" and R'" together with the Si or Ge atom form a cyclic group, preferably having 2 to 8 C atoms.

In another preferred embodiment, in the groups AR'R"R'" of formula II all substituents R', R" and R'" are identical.

In another preferred embodiment, in the groups AR'R"R'" of formula II at least two of the substituents R', R" and R'" are not identical. This means that at least one substituent R', R" and R'" has a meaning that is different from the meanings of the other substituents R', R" and R.

In another preferred embodiment, in the groups AR'R"R'" of formula II each of R', R" and R'" has a meaning that is different from the other of R" and R. Further preferred are groups AR'R"R'" of formula II wherein two of R', R" and R'" have the same meaning and one of R', R" and R'" has a meaning which is different from the other two of R', R" and R'".

Further preferred are groups AR'R"R'" of formula II, wherein one or more of R', R" and R'" denote or contain an alkenyl group or an aryl or heteroaryl group.

Very preferred are compounds of formula I wherein all of $X^1$ to $X^6$ are H.

In another preferred embodiment, in the compounds of formula I $X^1$, $X^2$, $X^3$, $X^4$, $X^5$ and $X^6$ are selected from the group consisting of H, F, Cl, Br, I, —CN, and straight chain, branched or cyclic alkyl, alkoxy, thioalkyl, alkenyl, alkynyl, alkylcarbonyl, alkoxycarbonyl, alkylcarbonyloxy, alkylcarbonylamido, alkylamidocarbonyl or alkoxycarbonyloxy with 1 to 20, preferably 1 to 12 C atoms which is unsubstituted or substituted with one or more F or Cl atoms or OH groups or perfluorinated.

In another preferred embodiment, in the compounds of formula I one or more of $X^1$, $X^2$, $X^3$, $X^4$, $X^5$ and $X^6$ are selected from the group consisting of aromatic and heteroaromatic groups with 4 to 25 ring atoms, which are mono- or polycyclic, i.e. which may also contain two or more individual rings that are connected to each other via single bonds, or contain two or more fused rings, and wherein each ring is unsubstituted or substituted with one or more groups L as defined above.

Very preferably these aforementioned aromatic and heteroaromatic groups are selected from the group consisting of phenyl, furan, thiophene, selenophene, N-pyrrole, pyridine, pyrimidine, thiazole, thiadiazole, oxazole, oxadiazole, selenazole, and bi-, tri- or tetracyclic aryl or heteroaryl groups containing one or more of the aforementioned rings and optionally one or more benzene rings, wherein the individual rings are connected by single bonds or fused with each other, and wherein all the aforementioned groups are unsubstituted, or substituted with one or more groups L as defined above.

Very preferably these aforementioned bi-, tri- or tetracyclic aryl or heteroaryl groups are selected from the group consisting of thieno[3,2-b]-thiophene, dithieno[3,2-b:2',3'-d]thiophene, selenopheno[3,2-b]selenophene-2,5-diyl, selenopheno[2,3-b]selenophene-2,5-diyl, selenopheno[3,2-b]thiophene-2,5-diyl, selenopheno[2,3-b]thiophene-2,5-diyl, benzo[1,2-b:4,5-b']dithiophene-2,6-diyl, 2,2-dithiophene, 2,2-diselenophene, dithieno-[3,2-b:2',3'-d]silole-5,5-diyl, 4H-cyclopenta[2,1-b:3,4-b']dithiophene-2,6-diyl, benzo[b]thiophene, benzo[b]selenophene, benzooxazole, benzo-thiazole, benzoselenazole, wherein all the aforementioned groups are unsubstituted, or substituted with one or more groups L as defined above.

Preferred compounds of formula I are selected from the following formula:

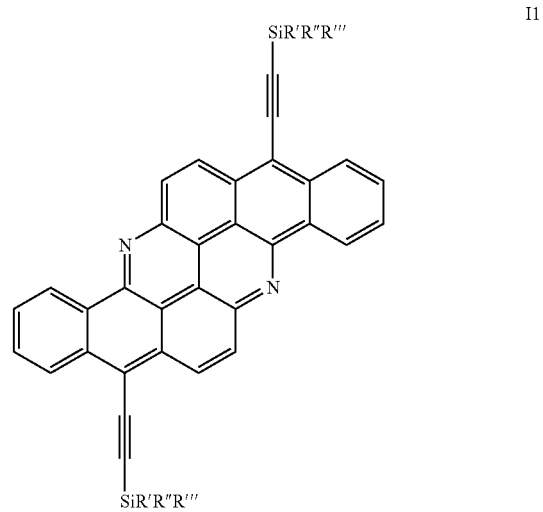

I1 wherein R', R" and R'" are as defined in formula II or have one of the preferred meanings as given above and below.

Above and below, an alkyl group or an alkoxy group, i.e. alkyl where the terminal $CH_2$ group is replaced by —O—, can be straight-chain or branched. It is preferably straight-chain, has 2, 3, 4, 5, 6, 7 or 8 carbon atoms and accordingly is preferably ethyl, propyl, butyl, pentyl, hexyl, heptyl, octyl, ethoxy, propoxy, butoxy, pentoxy, hexoxy, heptoxy, or octoxy, furthermore methyl, nonyl, decyl, undecyl, dodecyl, tridecyl, tetradecyl, pentadecyl, methoxy, nonoxy, decoxy, undecoxy, dodecoxy, tridecoxy or tetradecoxy, for example.

An alkenyl group, i.e. alkyl wherein one or more $CH_2$ groups are replaced by —CH=CH— can be straight-chain or branched. It is preferably straight-chain, has 2 to 10 C atoms and accordingly is preferably vinyl, prop-1-, or prop-2-enyl, but-1-, 2- or but-3-enyl, pent-1-, 2-, 3- or pent-4-enyl, hex-1-, 2-, 3-, 4- or hex-5-enyl, hept-1-, 2-, 3-, 4-, 5- or hept-6-enyl, oct-1-, 2-, 3-, 4-, 5-, 6- or oct-7-enyl, non-1-, 2-, 3-, 4-, 5-, 6-, 7- or non-8-enyl, dec-1-, 2-, 3-, 4-, 5-, 6-, 7-, 8- or dec-9-enyl.

Especially preferred alkenyl groups are $C_2$-$C_7$-1E-alkenyl, $C_4$-$C_7$-3E-alkenyl, $C_5$-$C_7$-4-alkenyl, $C_6$-$C_7$-5-alkenyl and $C_7$-6-alkenyl, in particular $C_2$-$C_7$-1E-alkenyl, $C_4$-$C_7$-3E-alkenyl and $C_5$-$C_7$-4-alkenyl. Examples for particularly preferred alkenyl groups are vinyl, 1E-propenyl, 1E-butenyl, 1E-pentenyl, 1E-hexenyl, 1E-heptenyl, 3-butenyl, 3E-pentenyl, 3E-hexenyl, 3E-heptenyl, 4-pentenyl, 4Z-hexenyl, 4E-hexenyl, 4Z-heptenyl, 5-hexenyl, 6-heptenyl and the like. Groups having up to 5 C atoms are generally preferred.

An oxaalkyl group, i.e. alkyl where a non-terminal $CH_2$ group is replaced by —O—, is preferably straight-chain 2-oxapropyl (=methoxymethyl), 2-(=ethoxymethyl) or 3-oxabutyl (=2-methoxyethyl), 2-, 3-, or 4-oxapentyl, 2-, 3-, 4-, or 5-oxahexyl, 2-, 3-, 4-, 5-, or 6-oxaheptyl, 2-, 3-, 4-, 5-, 6- or 7-oxaoctyl, 2-, 3-, 4-, 5-, 6-, 7- or 8-oxanonyl or 2-, 3-, 4-, 5-, 6-, 7-, 8- or 9-oxadecyl, for example.

In an alkyl group wherein one $CH_2$ group is replaced by —O— and another $CH_2$ group is replaced by —CO—, these radicals are preferably neighboured. Accordingly these radicals together form a carbonyloxy group -CO—O— or an oxycarbonyl group —O—CO—. Preferably this group is straight-chain and has 2 to 6 C atoms. It is accordingly preferably acetyloxy, propionyloxy, butyryloxy, pentanoyloxy, hexanoyloxy, acetyloxymethyl, propionyloxy-methyl, butyryloxymethyl, pentanoyloxymethyl, 2-acetyloxyethyl, 2-propionyloxyethyl, 2-butyryloxyethyl, 3-acetyloxypropyl, 3-propionyl-oxypropyl, 4-acetyloxybutyl, methoxycarbonyl, ethoxycarbonyl, propoxycarbonyl, butoxycarbonyl, pentoxycarbonyl, methoxycarbonyl-methyl, ethoxycarbonylmethyl, propoxycarbonylmethyl, butoxycarbonyl-methyl, 2-(methoxycarbonyl)ethyl, 2-(ethoxycarbonyl)ethyl, 2-(propoxycarbonyl)-ethyl, 3-(methoxycarbonyl)propyl, 3-(ethoxycarbonyl)propyl, 4-(methoxy-carbonyl)-butyl.

An alkyl group wherein two or more $CH_2$ groups are replaced by —O— and/or —COO— can be straight-chain or branched. It is preferably straight-chain and has 3 to 12 C atoms. Accordingly it is preferably bis-carboxy-methyl, 2,2-bis-carboxy-ethyl, 3,3-bis-carboxy-propyl, 4,4-bis-carboxy-butyl, 5,5-bis-carboxy-pentyl, 6,6-bis-carboxy-hexyl, 7,7-bis-carboxy-heptyl, 8,8-bis-carboxy-octyl, 9,9-bis-carboxy-nonyl, 10,10-bis-carboxy-decyl, bis-(methoxycarbonyl)-methyl, 2,2-bis-(methoxycarbonyl)-ethyl, 3,3-bis-(methoxycarbonyl)-propyl, 4,4-bis-(methoxycarbonyl)-butyl, 5,5-bis-(methoxycarbonyl)-pentyl, 6,6-bis-(methoxycarbonyl)-hexyl, 7,7-bis-(methoxycarbonyl)-heptyl, 8,8-bis-(methoxycarbonyl)-octyl, bis-(ethoxycarbonyl)-methyl, 2,2-bis-(ethoxycarbonyl)-ethyl, 3,3-bis-(ethoxycarbonyl)-propyl, 4,4-bis-(ethoxycarbonyl)-butyl, 5,5-bis-(ethoxycarbonyl)-hexyl.

A thioalkyl group, i.e where one $CH_2$ group is replaced by —S—, is preferably straight-chain thiomethyl (—$SCH_3$), 1-thioethyl (—$SCH_2CH_3$), 1-thiopropyl (=—$SCH_2CH_2CH_3$), 1-(thiobutyl), 1-(thiopentyl), 1-(thiohexyl), 1-(thioheptyl), 1-(thiooctyl), 1-(thiononyl), 1-(thiodecyl), 1-(thioundecyl) or 1-(thiododecyl), wherein preferably the $CH_2$ group adjacent to the $sp^2$ hybridised vinyl carbon atom is replaced.

$X^1$ to $X^6$, $R^1$ to $R^3$, R', R" and R''' can be an achiral or a chiral group. Particularly preferred chiral groups are 2-butyl (=1-methylpropyl), 2-methylbutyl, 2-methylpentyl, 3-methylpentyl, 2-ethylhexyl, 2-propylpentyl, in particular 2-methylbutyl, 2-methylbutoxy, 2-methylpentoxy, 3-methylpentoxy, 2-ethyl-hexoxy, 1-methylhexoxy, 2-octyloxy, 2-oxa-3-methylbutyl, 3-oxa-4-methyl-pentyl, 4-methylhexyl, 2-hexyl, 2-octyl, 2-nonyl, 2-decyl, 2-dodecyl, 6-methoxyoctoxy, 6-methyloctoxy, 6-methyloctanoyloxy, 5-methyl-heptyl-oxycarbonyl, 2-methylbutyryloxy, 3-methylvaleroyloxy, 4-methyl-hexanoyloxy, 2-chlorpropionyloxy, 2-chloro-3-methylbutyryloxy, 2-chloro-4-methyl-valeryloxy, 2-chloro-3-methylvaleryloxy, 2-methyl-3-oxapentyl, 2-methyl-3-oxahexyl, 1-methoxypropyl-2-oxy, 1-ethoxypropyl-2-oxy, 1-propoxypropyl-2-oxy, 1-butoxypropyl-2-oxy, 2-fluorooctyloxy, 2-fluorodecyl-oxy, 1,1,1-trifluoro-2-octyloxy, 1,1,1-trifluoro-2-octyl, 2-fluoromethyloctyloxy for example. Very preferred are 2-hexyl, 2-octyl, 2-octyloxy, 1,1,1-trifluoro-2-hexyl, 1,1,1-trifluoro-2-octyl and 1,1,1-trifluoro-2-octyloxy.

Preferred achiral branched groups are isopropyl, isobutyl (=methylpropyl),
isopentyl (=3-methylbutyl), tertiary butyl, isopropoxy, 2-methylpropoxy and 3-methylbutoxy.

—$CY^0$=$CY^{00}$— is preferably —CH=CH—, —CF=CF— or —CH=C(CN)—.

Halogen is F, Cl, Br or I, preferably F, Cl or Br.

L is preferably selected from P-Sp-, F, Cl, Br, I, —OH, —CN, —$NO_2$, —NCO, —NCS, —OCN, —SCN, —C(=O)$NR^0R^{00}$, —C(=O)$X^0$, —C(=O)$R^0$, —$NR^0R^{00}$, C(=O)OH, straight chain, branched or cyclic alkyl, alkoxy, oxaalkyl or thioalkyl with 1 to 20, preferably 1 to 12 C atoms which is unsubstituted or substituted with one or more F or Cl atoms or OH groups or perfluorinated, and straight chain, branched or cyclic alkenyl, alkynyl, alkylcarbonyl, alkoxycarbonyl, alkylcarbonyloxy or alkoxycarbonyloxy with 2 to 20, preferably 2 to 12 C atoms which is unsubstituted or substituted with one or more F or Cl atoms or OH groups or perfluorinated.

The compounds of formula I may also be substituted with a polymerisable or reactive group, which is optionally protected during the process of forming the polymer. Particular preferred compounds of this type are those of formula I that contain one or more substituents L which denote P-Sp, wherein P is a polymerisable or reactive group and Sp is a spacer group or a single bond. These compounds are particularly useful as semiconductors or charge transport materials, as they can be crosslinked via the groups P, for example by polymerisation in situ, during or after processing the polymer into a thin film for a semiconductor component, to yield crosslinked polymer films with high charge carrier mobility and high thermal, mechanical and chemical stability.

Preferably the polymerisable or reactive group P is selected from $CH_2$=$CW^1$—COO—, $CH_2$=$CW^1$—CO—,

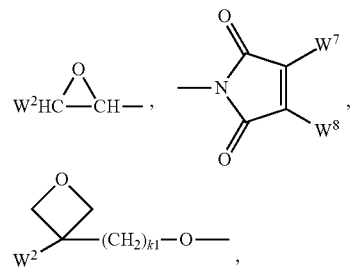

$CH_2$=$CW^2$—(O)$_{k1}$—, $CH_3$—CH=CH—O—, ($CH_2$=CH)$_2$CH—OCO—, ($CH_2$=CH—$CH_2$)$_2$CH—OCO—, ($CH_2$=CH—$CH_2$)$_2$CH—O—, ($CH_2$=CH—$CH_2$)$_2$N—, ($CH_2$=CH—$CH_2$)$_2$N—CO—, HO—$CW^2W^3$—, HS—$CW^2W^3$—, $HW^2$N—, HO—$CW^2W^3$—NH—, $CH_2$=$CW^1$—CO—NH—, $CH_2$=CH—(COO)$_{k1}$-Phe-(O)$_{k2}$—, $CH_2$=CH—(CO)$_{k1}$-Phe-(O)$_{k2}$—, Phe-CH=CH—, HOOC—, OCN—, and $W^4W^5W^6$Si—, with $W^1$ being H, F, Cl, CN, $CF_3$, phenyl or alkyl with 1 to 5 C-atoms, in particular H, Cl or $CH_3$, $W^2$ and $W^3$ being independently of each other H or alkyl with 1 to 5 C-atoms, in particular H, methyl, ethyl or n-propyl, $W^4$, $W^5$ and $W^6$ being independently of each other Cl, oxaalkyl or oxacarbonylalkyl with 1 to 5 C-atoms, $W^7$ and $W^8$ being independently of each other H, Cl or alkyl with 1 to 5 C-atoms, Phe being 1,4-phenylene that is optionally substituted by one or more groups L as defined above, and $k_1$ and $k_2$ being independently of each other 0 or 1.

Alternatively P is a protected derivative of these groups which is non-reactive under the conditions described for the process according to the present invention. Suitable protective groups are known to the ordinary expert and described in the literature, for example in Green, "Protective Groups in Organic Synthesis", John Wiley and Sons, New York (1981), like for example acetals or ketals.

Especially preferred groups P are $CH_2$=CH—COO—, $CH_2$=C($CH_3$)—COO—, $CH_2$=CH—, $CH_2$=CH—O—, ($CH_2$=CH)$_2$CH—OCO—, ($CH_2$=CH)$_2$CH—O—,

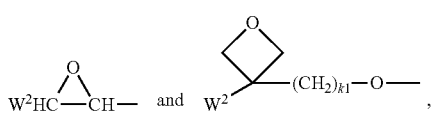

or protected derivatives thereof.

Polymerisation of group P can be carried out according to methods that are known to the ordinary expert and described in the literature, for example in D. J. Broer; G. Challa; G. N. Mol, *Macromol. Chem.*, 1991, 192, 59.

The term "spacer group" is known in prior art and suitable spacer groups Sp are known to the ordinary expert (see e.g. Pure Appl. Chem. 73(5), 888 (2001). The spacer group Sp is preferably of formula Sp'-X', such that P-Sp- is P-Sp'-X'—, wherein Sp' is alkylene with up to 30 C atoms which is unsubstituted or mono- or polysubstituted by F, Cl, Br, I or CN, it being also possible for one or more non-adjacent $CH_2$ groups to be replaced, in each case independently from one another, by —O—, —S—, —NH—, —$NR^0$—, —$SiR^0R^{00}$—, —CO—, —COO—, —OCO—, —OCO—O—, —S—CO—, —CO—S—, —CH=CH— or —C≡C— in such a manner that O and/or S atoms are not linked directly to one another, X' is —O—, —S—, —CO—, —COO—, —OCO—, —O—COO—, —CO—$NR^0$—, —$NR^0$—CO—, —$NR^0$—CO—$NR^{00}$—, —$OCH_2$—, —$CH_2O$—, —$SCH_2$—, —$CH_2S$—, —$CF_2O$—, —$OCF_2$—, —$CF_2S$—, —$SCF_2$—, —$CF_2CH_2$—, —$CH_2CF_2$—, —$CF_2CF_2$—, —CH=N—, —N=CH—, —N=N—, —CH=$CR^0$—, —$CY^0$=$CY^{00}$—, —C≡C—, —CH=CH—COO—, —OCO—CH=CH— or a single bond, $R^0$ and $R^{00}$ are independently of each other H or alkyl with 1 to 12 C-atoms, and $Y^0$ and $Y^{00}$ are independently of each other H, F, Cl or CN.

X' is preferably —O—, —S—, —$OCH_2$—, —$CH_2O$—, —$SCH_2$—, —$CH_2S$—, —$CF_2O$—, —$OCF_2$—, —$CF_2S$—, —$SCF_2$—, —$CH_2CH_2$—, —$CF_2CH_2$—, —$CH_2CF_2$—, —$CF_2CF_2$—, —CH=N—, —N=CH—, —N=N—, —CH=$CR^0$—, —$CY^0$=$CY^{00}$—, —C≡C— or a single bond, in particular —O—, —S—, —C≡C—, —$CY^0$=$CY^{00}$— or a single bond. In another preferred embodiment X' is a group that is able to form a conjugated system, such as —C≡C— or —$CY^0$=$CY^{00}$—, or a single bond.

Typical groups Sp' are, for example, —$(CH_2)_p$—, —$(CH_2CH_2O)_q$—$CH_2CH_2$—, —$CH_2CH_2$—S—$CH_2CH_2$— or —$CH_2CH_2$—NH—$CH_2CH_2$— or —$(SiR^0R^{00}$—O$)_p$—, with p being an integer from 2 to 12, q being an integer from 1 to 3 and $R^0$ and $R^{00}$ having the meanings given above.

Preferred groups Sp' are ethylene, propylene, butylene, pentylene, hexylene, heptylene, octylene, nonylene, decylene, undecylene, dodecylene, octadecylene, ethyleneoxyethylene, methyleneoxybutylene, ethylene-thioethylene, ethylene-N-methyl-iminoethylene, 1-methylalkylene, ethenylene, propenylene and butenylene for example.

The compounds of formula I can be synthesized according to or in analogy to methods that are known to the skilled person and are described in the literature. Other methods of preparation can be taken from the examples. Especially preferred and suitable synthesis methods are further described below.

A suitable and preferred synthesis route for a soluble benzo[h]benz[5,6]-acridino[2,1,9,8-klmna]acridine (flavanthrene) is exemplarily shown in Scheme 1 below for a flavanthrene that is disubstituted with (butyldiiso-propyl)silylethynyl groups.

Dichlorodiisopropylsilane 1 is treated with n-butyllithium in tetrahydrofuran solution to yield butyldiisopropyl-chlorosilane 2, which is then reacted with lithium (trimethylsilyl)acetylide in situ to yield trimethylsilyl protected ethynyl butyldiisopropylsilane 3. Selective removal of the TMS group with potassium carbonate affords ethynyl butyldiisopropylsilane 4. Using a standard procedure, this ethynyl silane is lithiated with n-butyllithium then reacted with commercial flavanthrone to yield the diol intermediate 5, which is reductive-aromatized under acidic conditions to afford 6.

Further derivatives with different substituents can be synthesised in analogous manner.

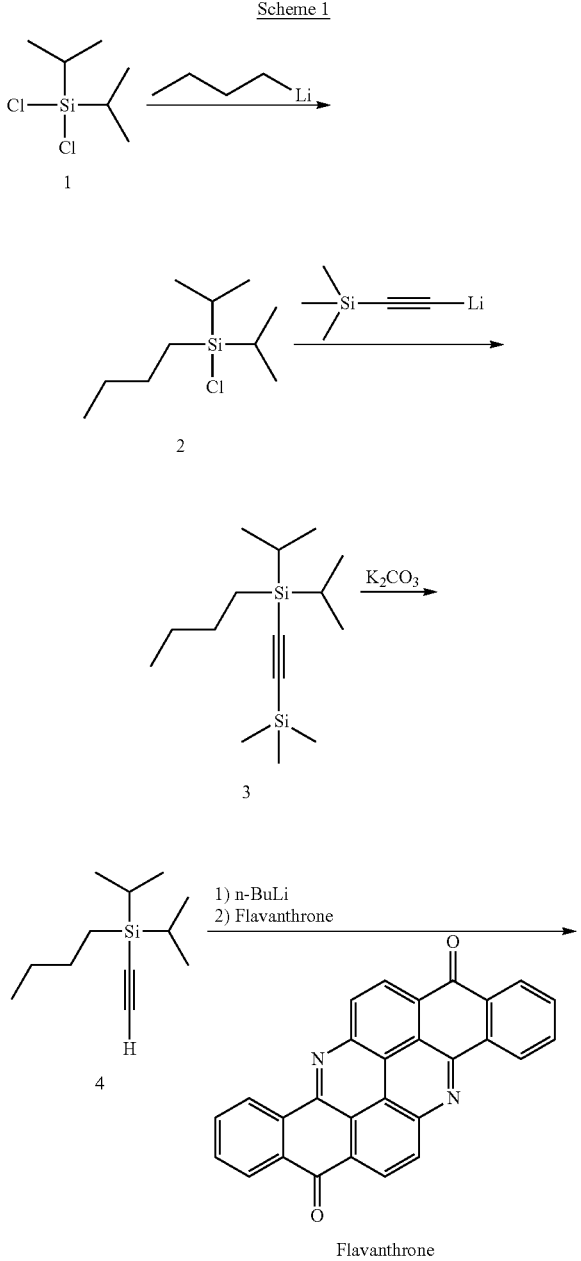

Scheme 1

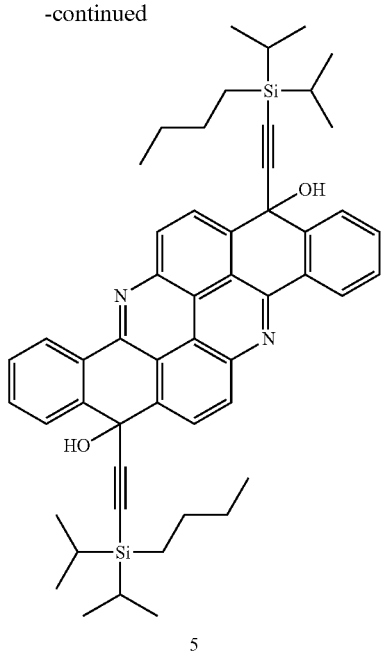

KI, NaH$_2$PO$_2$ in HOAc

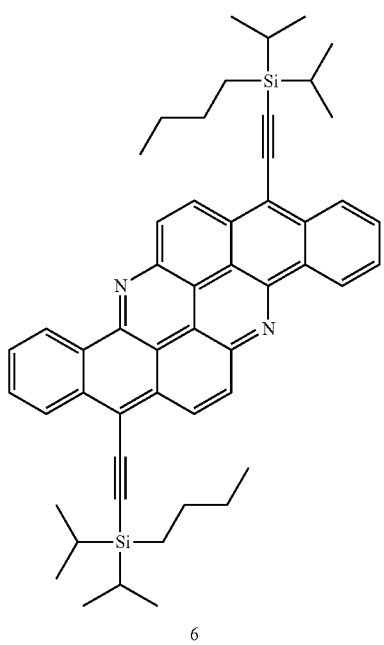

The invention further relates to a formulation comprising one or more compounds of formula I and one or more solvents, preferably selected from organic solvents.

Preferred solvents are aliphatic hydrocarbons, chlorinated hydrocarbons, aromatic hydrocarbons, ketones, ethers and mixtures thereof. Additional solvents which can be used include 1,2,4-trimethylbenzene, 1,2,3,4-tetra-methyl benzene, pentylbenzene, mesitylene, cumene, cymene, cyclohexylbenzene, diethylbenzene, tetralin, decalin, 2,6-lutidine, 2-fluoro-m-xylene, 3-fluoro-o-xylene, 2-chlorobenzotrifluoride, dimethylformamide, 2-chloro-6fluorotoluene, 2-fluoroanisole, anisole, 2,3-dimethylpyrazine, 4-fluoroanisole, 3-fluoroanisole, 3-trifluoro-methylanisole, 2-methylanisole, phenetol, 4-methylansiole, 3-methylanisole, 4-fluoro-3-methylanisole, 2-fluorobenzonitrile, 4-fluoroveratrol, 2,6-dimethylanisole, 3-fluorobenzonitrile, 2,5-dimethylanisole, 2,4-dimethylanisole, benzonitrile, 3,5-dimethylanisole, N,N-dimethylaniline, ethyl benzoate, 1-fluoro-3,5-dimethoxybenzene, 1-methylnaphthalene, N-methylpyrrolidinone, 3-fluorobenzotrifluoride, benzotrifluoride, benzotrifluoride, diosane, trifluoromethoxy-benzene, 4-fluorobenzotrifluoride, 3-fluoropyridine, toluene, 2-fluorotoluene, 2-fluorobenzotrifluoride, 3-fluorotoluene, 4-isopropylbiphenyl, phenyl ether, pyridine, 4-fluorotoluene, 2,5-difluorotoluene, 1-chloro-2,4-difluorobenzene, 2-fluoropyridine, 3-chlorofluorobenzene, 3-chlorofluorobenzene, 1-chloro-2,5-difluorobenzene, 4-chlorofluorobenzene, chloro-benzene, o-dichlorobenzene, 2-chlorofluorobenzene, p-xylene, m-xylene, o-xylene or mixture of o-, m-, and p-isomers. Solvents with relatively low polarity are generally preferred. For inkjet printing solvents with high boiling temperatures and solvent mixtures are preferred. For spin coating alkylated benzenes like xylene and toluene are preferred.

The invention further relates to an organic semiconducting formulation comprising one or more compounds of formula I, one or more organic binders, or precursors thereof, preferably having a permittivity ∈ at 1,000 Hz of 3.3 or less, and optionally one or more solvents.

Combining specified soluble compounds of formula I, especially compounds of the preferred formulae as described above and below, with an organic binder resin (hereinafter also referred to as "the binder") results in little or no reduction in charge mobility of the compounds of formula I, even an increase in some instances. For instance, the compounds of formula I may be dissolved in a binder resin (for example poly(α-methylstyrene) and deposited (for example by spin coating), to form an organic semiconducting layer yielding a high charge mobility. Moreover, a semiconducting layer formed thereby exhibits excellent film forming characteristics and is particularly stable.

If an organic semiconducting layer formulation of high mobility is obtained by combining a compound of formula I with a binder, the resulting formulation leads to several advantages. For example, since the compounds of formula I are soluble they may be deposited in a liquid form, for example from solution. With the additional use of the binder the formulation can be coated onto a large area in a highly uniform manner. Furthermore, when a binder is used in the formulation it is possible to control the properties of the formulation to adjust to printing processes, for example viscosity, solid content, surface tension. Whilst not wishing to be bound by any particular theory it is also anticipated that the use of a binder in the formulation fills in volume between crystalline grains otherwise being void, making the organic semiconducting layer less sensitive to air and moisture. For example, layers formed according to the process of the present invention show very good stability in OFET devices in air.

The invention also provides an organic semiconducting layer which comprises the organic semiconductor or the organic semiconducting layer formulation.

The invention further provides a process for preparing an organic semiconducting layer, said process comprising the following steps:

(i) depositing on a substrate a liquid layer of a formulation comprising one or more compounds of formula I as described above and below, one or more organic binder resins or precursors thereof, and optionally one or more solvents, (ii) forming from the liquid layer a solid layer which is the organic semiconducting layer, (iii) optionally removing the layer from the substrate.

The process is described in more detail below.

The invention additionally provides an electronic device comprising the said organic semiconducting layer. The electronic device may include, without limitation, an organic field effect transistor (OFET), organic light emitting diode (OLED), photodetector, sensor, logic circuit, memory element, capacitor or photovoltaic (PV) cell. For example, the active semiconductor channel between the drain and source in an OFET may comprise the layer of the invention. As another example, a charge (hole or electron) injection or transport layer in an OLED device may comprise the layer of the invention. The formulations according to the present invention and layers formed therefrom have particular utility in OFETs especially in relation to the preferred embodiments described herein.

The semiconducting compound of formula I preferably has a charge carrier mobility, $\mu$, of more than $0.001\ cm^2V^{-1}s^{-1}$, very preferably of more than $0.01\ cm^2V^{-1}s^{-1}$, especially preferably of more than $0.1\ cm^2V^{-1}s^{-1}$ and most preferably of more than $0.5\ cm^2V^{-1}s^{-1}$.

The binder, which is typically a polymer, may comprise either an insulating binder or a semiconducting binder, or mixtures thereof may be referred to herein as the organic binder, the polymeric binder or simply the binder.

Preferred binders according to the present invention are materials of low permittivity, that is, those having a permittivity $\in$ at 1,000 Hz of 3.3 or less. The organic binder preferably has a permittivity $\in$ at 1,000 Hz of 3.0 or less, more preferably 2.9 or less. Preferably the organic binder has a permittivity $\in$ at 1,000 Hz of 1.7 or more. It is especially preferred that the permittivity of the binder is in the range from 2.0 to 2.9. Whilst not wishing to be bound by any particular theory it is believed that the use of binders with a permittivity $\in$ of greater than 3.3 at 1,000 Hz, may lead to a reduction in the OSC layer mobility in an electronic device, for example an OFET. In addition, high permittivity binders could also result in increased current hysteresis of the device, which is undesirable.

An example of a suitable organic binder is polystyrene. Further examples of suitable binders are disclosed for example in US 2007/0102696 A1. Especially suitable and preferred binders are described in the following.

In one type of preferred embodiment, the organic binder is one in which at least 95%, more preferably at least 98% and especially all of the atoms consist of hydrogen, fluorine and carbon atoms.

It is preferred that the binder normally contains conjugated bonds, especially conjugated double bonds and/or aromatic rings.

The binder should preferably be capable of forming a film, more preferably a flexible film. Polymers of styrene and α-methyl styrene, for example copolymers including styrene, α-methylstyrene and butadiene may suitably be used.

Binders of low permittivity of use in the present invention have few permanent dipoles which could otherwise lead to random fluctuations in molecular site energies. The permittivity $\in$ (dielectric constant) can be determined by the ASTM D150 test method.

It is also preferred that in the present invention binders are used which have solubility parameters with low polar and hydrogen bonding contributions as materials of this type have low permanent dipoles. A preferred range for the solubility parameters ('Hansen parameter') of a binder for use in accordance with the present invention is provided in Table 1 below.

TABLE 1

| | Hansen parameter | | |
|---|---|---|---|
| | $\delta_d\ MPa^{1/2}$ | $\delta_p\ MPa^{1/2}$ | $\delta_h\ MPa^{1/2}$ |
| Preferred range | 14.5+ | 0-10 | 0-14 |
| More preferred range | 16+ | 0-9 | 0-12 |
| Most preferred range | 17+ | 0-8 | 0-10 |

The three dimensional solubility parameters listed above include: dispersive ($\delta_d$), polar ($\delta_p$) and hydrogen bonding ($\delta_h$) components (C. M. Hansen, Ind. Eng. and Chem., Prod. Res. and Devl., 9, No 3, p 282., 1970). These parameters may be determined empirically or calculated from known molar group contributions as described in Handbook of Solubility Parameters and Other Cohesion Parameters ed. A. F. M. Barton, CRC Press, 1991. The solubility parameters of many known polymers are also listed in this publication.

It is desirable that the permittivity of the binder has little dependence on frequency. This is typical of non-polar materials. Polymers and/or copolymers can be chosen as the binder by the permittivity of their substituent groups. A list of suitable and preferred low polarity binders is given (without limiting to these examples) in Table 2:

TABLE 2

| Binder | typical low frequency permittivity ($\epsilon$) |
|---|---|
| polystyrene | 2.5 |
| poly(α-methylstyrene) | 2.6 |
| poly(α-vinylnaphtalene) | 2.6 |
| poly(vinyltoluene) | 2.6 |
| polyethylene | 2.2-2.3 |
| cis-polybutadiene | 2.0 |
| polypropylene | 2.2 |
| poly(4-methyl-1-pentene) | 2.1 |
| poly (4-methylstyrene) | 2.7 |
| poly(chorotrifluoroethylene) | 2.3-2.8 |
| poly(2-methyl-1,3-butadiene) | 2.4 |
| poly(p-xylylene) | 2.6 |
| poly(α-α-α'-α' tetrafluoro-p-xylylene) | 2.4 |
| poly[1,1-(2-methyl propane)bis(4-phenyl)carbonate] | 2.3 |
| poly(cyclohexyl methacrylate) | 2.5 |
| poly(chlorostyrene) | 2.6 |
| poly(2,6-dimethyl-1,4-phenylene ether) | 2.6 |
| polyisobutylene | 2.2 |
| poly(vinyl cyclohexane) | 2.2 |
| poly(vinylcinnamate) | 2.9 |
| poly(4-vinylbiphenyl) | 2.7 |

Further preferred binders are poly(1,3-butadiene) and polyphenylene.

Especially preferred are formulations wherein the binder is selected from poly-α-methyl styrene, polystyrene and polytriarylamine or any copolymers of these, and the solvent is selected from xylene(s), toluene, tetralin and cyclohexanone.

Copolymers containing the repeat units of the above polymers are also suitable as binders. Copolymers offer the possibility of improving compatibility with the compounds of formula I, modifying the morphology and/or the glass transition temperature of the final layer composition. It will be appreciated that in the above table certain materials are insoluble in commonly used solvents for preparing the layer. In these cases analogues can be used as copolymers. Some examples of copolymers are given in Table 3 (without limiting to these examples). Both random or block copolymers can be used. It is also possible to add more polar monomer components as long as the overall composition remains low in polarity.

TABLE 3

| Binder | typical low frequency permittivity (ε) |
|---|---|
| poly(ethylene/tetrafluoroethylene) | 2.6 |
| poly(ethylene/chlorotrifluoroethylene) | 2.3 |
| fluorinated ethylene/propylene copolymer | 2-2.5 |
| polystyrene-co-α-methylstyrene | 2.5-2.6 |
| ethylene/ethyl acrylate copolymer | 2.8 |
| poly(styrene/10% butadiene) | 2.6 |
| poly(styrene/15% butadiene) | 2.6 |
| poly(styrene/2,4 dimethylstyrene) | 2.5 |
| Topas ™ (all grades) | 2.2-2.3 |

Other copolymers may include: branched or non-branched polystyrene-block-polybutadiene, polystyrene-block(polyethylene-ran-butylene)-block-polystyrene, polystyrene-block-polybutadiene-block-polystyrene, polystyrene-(ethylene-propylene)-diblock-copolymers (e.g. KRATON®-G1701E, Shell), poly(propylene-co-ethylene) and poly(styrene-co-methylmethacrylate).

Preferred insulating binders for use in the organic semiconductor layer formulation according to the present invention are poly(α-methylstyrene), polyvinylcinnamate, poly(4-vinylbiphenyl), poly(4-methylstyrene), and Topas™ 8007 (linear olefin, cyclo-olefin(norbornene) copolymer available from Ticona, Germany). Most preferred insulating binders are poly(α-methylstyrene), polyvinylcinnamate and poly(4-vinylbiphenyl).

The binder can also be selected from crosslinkable binders, like e.g. acrylates, epoxies, vinylethers, thiolenes etc., preferably having a sufficiently low permittivity, very preferably of 3.3 or less. The binder can also be mesogenic or liquid crystalline.

As mentioned above the organic binder may itself be a semiconductor, in which case it will be referred to herein as a semiconducting binder. The semiconducting binder is still preferably a binder of low permittivity as herein defined. Semiconducting binders for use in the present invention preferably have a number average molecular weight ($M_n$) of at least 1500-2000, more preferably at least 3000, even more preferably at least 4000 and most preferably at least 5000. The semiconducting binder preferably has a charge carrier mobility, μ, of at least $10^{-5}$ cm$^2$V$^{-1}$s$^{-1}$, more preferably at least $10^{-4}$ cm$^2$V$^{-1}$s$^{-1}$.

A preferred class of semiconducting binder is a polymer as disclosed in U.S. Pat. No. 6,630,566, preferably an oligomer or polymer having repeat units of formula 1:

$$-\!\!\left[Ar^{11}\!-\!\overset{Ar^{33}}{\underset{|}{N}}\!-\!Ar^{22}\right]_{\!m}\!\!- \qquad 1$$

wherein
Ar$^{11}$, Ar$^{22}$ and Ar$^{33}$ which may be the same or different, denote, independently if in different repeat units, an optionally substituted aromatic group that is mononuclear or polynuclear, and
m is an integer≥1, preferably ≥6, preferably ≥10, more preferably ≥15 and most preferably ≥20.

In the context of Ar$^{11}$, Ar$^{22}$ and Ar$^{33}$, a mononuclear aromatic group has only one aromatic ring, for example phenyl or phenylene. A polynuclear aromatic group has two or more aromatic rings which may be fused (for example napthyl or naphthylene), individually covalently linked (for example biphenyl) and/or a combination of both fused and individually linked aromatic rings. Preferably each Ar$^{11}$, Ar$^{22}$ and Ar$^{33}$ is an aromatic group which is substantially conjugated over substantially the whole group.

Further preferred classes of semiconducting binders are those containing substantially conjugated repeat units. The semiconducting binder polymer may be a homopolymer or copolymer (including a block-copolymer) of the general formula 2:

$$A_{(c)}B_{(d)}\ldots Z_{(z)} \qquad 2$$

wherein A, B, . . . , Z each represent a monomer unit and (c), (d), . . . (z) each represent the mole fraction of the respective monomer unit in the polymer, that is each (c), (d), . . . (z) is a value from 0 to 1 and the total of (c)+(d)+ . . . + (z)=1.

Examples of suitable and preferred monomer units A, B, . . . Z include units of formula 1 above and of formulae 3 to 8 given below (wherein m is as defined in formula 1:

wherein m is as defined above and
R$^a$ and R$^b$ are independently of each other selected from H, F, CN, NO$_2$,
—N(R$^c$)(R$^d$) or optionally substituted alkyl, alkoxy, thioalkyl, acyl, aryl,
R$^c$ and R$^d$ are independently or each other selected from H, optionally substituted alkyl, aryl, alkoxy or polyalkoxy or other substituents,
and wherein the asterisk (*) is any terminal or end capping group including H, and the alkyl and aryl groups are optionally fluorinated;

wherein m is as defined above and
Y is Se, Te, O, S or —N(R$^e$)—, preferably O, S or —N(R$^e$)—,
R$^e$ is H, optionally substituted alkyl or optionally substituted aryl,
R$^a$ and R$^b$ are as defined in formula 3;

wherein R$^a$, R$^b$ and Y are as defined in formulae 3 and 4 and m is as defined in formula 1;

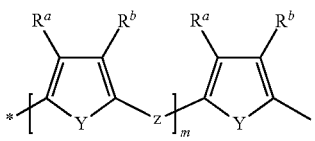

wherein $R^a$, $R^b$ and Y are as defined in formulae 3 and 4 and m is as defined in formula 1, Z is —C($T^1$)=C($T^2$)-, —C≡C—, —N($R^f$)—, —N=N—, ($R^f$)=N—, —N=C($R^f$)—, $T^1$ and $T^2$ independently of each other denote H, Cl, F, —CN or alkyl with 1 to 8 C atoms, $R^f$ is H or optionally substituted alkyl or aryl;

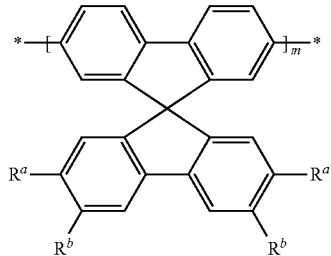

wherein $R^a$ and $R^b$ are as defined in formula 3 and m is as defined in formula 1;

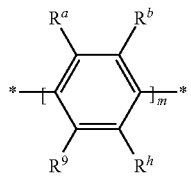

wherein $R^a$, $R^b$, $R^g$ and $R^h$ independently of each other have one of the meanings of $R^a$ and $R^b$ in formula 3 and m is as defined in formula 1.

In the case of the polymeric formulae described herein, such as formulae 1 to 8, the polymers may be terminated by any terminal group, that is any end-capping or leaving group, including H.

In the case of a block-copolymer, each monomer A, B, . . . Z may be a conjugated oligomer or polymer comprising a number, for example 2 to 50, of the units of formulae 3-8. The semiconducting binder preferably includes: arylamine, fluorene, thiophene, spirobifluorene and/or optionally substituted aryl (for example phenylene) groups, more preferably arylamine, most preferably triarylamine groups. The aforementioned groups may be linked by further conjugating groups, for example vinylene.

In addition, it is preferred that the semiconducting binder comprises a polymer (either a homo-polymer or copolymer, including block-copolymer) containing one or more of the aforementioned arylamine, fluorene, thiophene and/or optionally substituted aryl groups. A preferred semiconducting binder comprises a homo-polymer or copolymer (including block-copolymer) containing arylamine (preferably triarylamine) and/or fluorene units. Another preferred semiconducting binder comprises a homo-polymer or copolymer (including block-copolymer) containing fluorene and/or thiophene units.

The semiconducting binder may also contain carbazole or stilbene repeat units. For example, polyvinylcarbazole, polystilbene or their copolymers may be used. The semiconducting binder may optionally contain DBBDT segments (for example repeat units as described for formula 1 above) to improve compatibility with the soluble compounds of formula.

Very preferred semiconducting binders for use in the organic semiconductor formulation according to the present invention are poly(9-vinylcarbazole) and PTAA1, a polytriarylamine of the following formula

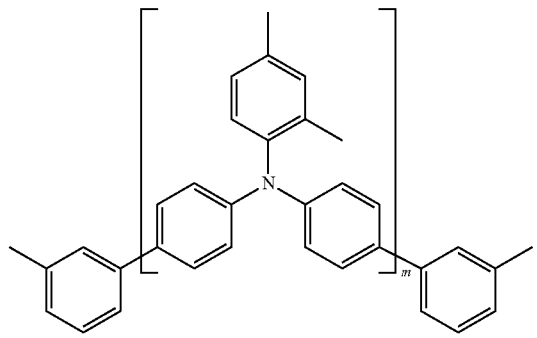

wherein m is as defined in formula 1.

For application of the semiconducting layer in p-channel FETs, it is desirable that the semiconducting binder should have a higher ionisation potential than the semiconducting compound of formula I, otherwise the binder may form hole traps. In n-channel materials the semiconducting binder should have lower electron affinity than the n-type semiconductor to avoid electron trapping.

The formulation according to the present invention may be prepared by a process which comprises:
(i) first mixing a compound of formula I and an organic binder or a precursor thereof. Preferably the mixing comprises mixing the two components together in a solvent or solvent mixture,
(ii) applying the solvent(s) containing the compound of formula I and the organic binder to a substrate; and optionally evaporating the solvent(s) to form a solid organic semiconducting layer according to the present invention,
(iii) and optionally removing the solid layer from the substrate or the substrate from the solid layer.

In step (i) the solvent may be a single solvent or the compound of formula I and the organic binder may each be dissolved in a separate solvent followed by mixing the two resultant solutions to mix the compounds.

The binder may be formed in situ by mixing or dissolving a compound of formula I in a precursor of a binder, for example a liquid monomer, oligomer or crosslinkable polymer, optionally in the presence of a solvent, and depositing the mixture or solution, for example by dipping, spraying, painting or printing it, on a substrate to form a liquid layer and then curing the liquid monomer, oligomer or crosslinkable polymer, for example by exposure to radiation, heat or electron beams, to produce a solid layer. If a preformed binder is used it may be dissolved together with the compound of formula I in a suitable solvent, and the solution deposited for example by dipping, spraying, painting or printing it on a substrate to form a liquid layer and then removing the solvent to leave a solid layer. It will be appreciated that solvents are chosen which are able to dissolve both the binder and the compound of formula I, and which upon evaporation from the solution blend give a coherent defect free layer.

Suitable solvents for the binder or the compound of formula I can be determined by preparing a contour diagram for the material as described in ASTM Method D 3132 at the concentration at which the mixture will be employed. The material is added to a wide variety of solvents as described in the ASTM method.

It will also be appreciated that in accordance with the present invention the formulation may also comprise two or more compounds of formula I and/or two or more binders or binder precursors, and that the process for preparing the formulation may be applied to such formulations.

Examples of suitable and preferred organic solvents include, without limitation, dichloromethane, trichloromethane, monochlorobenzene, o-dichlorobenzene, tetrahydrofuran, anisole, morpholine, toluene, o-xylene, m-xylene, p-xylene, 1,4-dioxane, acetone, methylethylketone, 1,2-dichloroethane, 1,1,1-trichloroethane, 1,1,2,2-tetrachloroethane, ethyl acetate, n-butyl acetate, dimethylformamide, dimethylacetamide, dimethylsulfoxide, tetralin, decalin, indane and/or mixtures thereof.

After the appropriate mixing and ageing, solutions are evaluated as one of the following categories: complete solution, borderline solution or insoluble. The contour line is drawn to outline the solubility parameter-hydrogen bonding limits dividing solubility and insolubility. 'Complete' solvents falling within the solubility area can be chosen from literature values such as published in "Crowley, J. D., Teague, G. S. Jr and Lowe, J. W. Jr., *Journal of Paint Technology*, 1966, 38(496), 296". Solvent blends may also be used and can be identified as described in "Solvents, W.H. Ellis, Federation of Societies for Coatings Technology, p 9-10, 1986". Such a procedure may lead to a blend of 'non' solvents that will dissolve both the binder and the compound of formula I, although it is desirable to have at least one true solvent in a blend.

Especially preferred solvents for use in the formulation according to the present invention, with insulating or semi-conducting binders and mixtures thereof, are xylene(s), toluene, tetralin and o-dichlorobenzene.

The proportions of binder to the compound of formula I in the formulation or layer according to the present invention are typically 20:1 to 1:20 by weight, preferably 10:1 to 1:10 more preferably 5:1 to 1:5, still more preferably 3:1 to 1:3 further preferably 2:1 to 1:2 and especially 1:1. Surprisingly and beneficially, dilution of the compound of formula I in the binder has been found to have little or no detrimental effect on the charge mobility, in contrast to what would have been expected from the prior art.

In accordance with the present invention it has further been found that the level of the solids content in the organic semiconducting layer formulation is also a factor in achieving improved mobility values for electronic devices such as OFETs. The solids content of the formulation is commonly expressed as follows:

$$\text{Solids content (\%)} = \frac{a+b}{a+b+c} \times 100$$

wherein a=mass of compound of formula I, b=mass of binder and c=mass of solvent.

The solids content of the formulation is preferably 0.1 to 10% by weight, more preferably 0.5 to 5% by weight.

The compounds according to the present invention can also be used in mixtures or blends, for example together with other compounds having charge-transport, semiconducting, electrically conducting, photoconducting and/or light emitting semiconducting properties. Thus, another aspect of the invention relates to a mixture or blend comprising one or more compounds of formula I and one or more further compounds having one or more of the above-mentioned properties. These mixtures can be prepared by conventional methods that are described in prior art and known to the skilled person. Typically the compounds are mixed with each other or dissolved in suitable solvents and the solutions combined.

The formulations according to the present invention can additionally comprise one or more further components like for example surface-active compounds, lubricating agents, wetting agents, dispersing agents, hydrophobing agents, adhesive agents, flow improvers, defoaming agents, deaerators, diluents which may be reactive or non-reactive, auxiliaries, colourants, dyes or pigments, sensitizers, stabilizers, nanoparticles or inhibitors.

It is desirable to generate small structures in modern microelectronics to reduce cost (more devices/unit area), and power consumption. Patterning of the layer of the invention may be carried out by photolithography or electron beam lithography.

Liquid coating of organic electronic devices such as field effect transistors is more desirable than vacuum deposition techniques. The formulations of the present invention enable the use of a number of liquid coating techniques. The organic semiconductor layer may be incorporated into the final device structure by, for example and without limitation, dip coating, spin coating, ink jet printing, letter-press printing, screen printing, doctor blade coating, roller printing, reverse-roller printing, offset lithography printing, flexographic printing, web printing, spray coating, brush coating or pad printing. The present invention is particularly suitable for use in spin coating the organic semiconductor layer into the final device structure.

Selected formulations of the present invention may be applied to prefabricated device substrates by ink jet printing or microdispensing. Preferably industrial piezoelectric print heads such as but not limited to those supplied by Aprion, Hitachi-Koki, InkJet Technology, On Target Technology, Picojet, Spectra, Trident, Xaar may be used to apply the organic semiconductor layer to a substrate. Additionally semi-industrial heads such as those manufactured by Brother, Epson, Konica, Seiko Instruments Toshiba TEC or single nozzle microdispensers such as those produced by Microdrop and Microfab may be used.

In order to be applied by ink jet printing or microdispensing, the mixture of the compound of formula I and the binder should be first dissolved in a suitable solvent. Solvents must fulfil the requirements stated above and must not have any detrimental effect on the chosen print head.

Additionally, solvents should have boiling points >100° C., preferably >140° C. and more preferably >150° C. in order to prevent operability problems caused by the solution drying out inside the print head. Suitable solvents include substituted and non-substituted xylene derivatives, di-$C_{1-2}$-alkyl formamide, substituted and non-substituted anisoles and other phenol-ether derivatives, substituted heterocycles such as substituted pyridines, pyrazines, pyrimidines, pyrrolidinones, substituted and non-substituted N,N-di-$C_{1\text{-}2}$-alkylanilines and other fluorinated or chlorinated aromatics.

A preferred solvent for depositing a formulation according to the present invention by ink jet printing comprises a benzene derivative which has a benzene ring substituted by one or more substituents wherein the total number of carbon atoms among the one or more substituents is at least three. For example, the benzene derivative may be substituted with a propyl group or three methyl groups, in either case there being at least three carbon atoms in total. Such a solvent enables an ink jet fluid to be formed comprising the solvent with the binder and the compound of formula I which reduces or prevents clogging of the jets and separation of the components during spraying. The solvent(s) may include those selected from the following list of examples: dodecylbenzene, 1-methyl-4-tert-butylbenzene, terpineol limonene, isodurene, terpinolene, cymene, diethylbenzene. The solvent may be a solvent mixture, that is a combination of two or more solvents, each solvent preferably having a boiling point>100° C., more preferably >140° C. Such solvent(s) also enhance film formation in the layer deposited and reduce defects in the layer.

The ink jet fluid (that is mixture of solvent, binder and semiconducting compound) preferably has a viscosity at 20° C. of 1 to 100 mPa·s, more preferably 1 to 50 mPa·s and most preferably 1 to 30 mPa·s.

The use of the binder in the present invention allows tuning the viscosity of the coating solution, to meet the requirements of particular print heads.

The semiconducting layer of the present invention is typically at most 1 micron (=1 μm) thick, although it may be thicker if required. The exact thickness of the layer will depend, for example, upon the requirements of the electronic device in which the layer is used. For use in an OFET or OLED, the layer thickness may typically be 500 nm or less.

In the semiconducting layer of the present invention there may be used two or more different compounds of formula I. Additionally or alternatively, in the semiconducting layer there may be used two or more organic binders of the present invention.

As mentioned above, the invention further provides a process for preparing the organic semiconducting layer which comprises (i) depositing on a substrate a liquid layer of a formulation which comprises one or more compounds of formula I, one or more organic binders or precursors thereof and optionally one or more solvents, and (ii) forming from the liquid layer a solid layer which is the organic semiconducting layer.

In the process, the solid layer may be formed by evaporation of the solvent and/or by reacting the binder resin precursor (if present) to form the binder resin in situ. The substrate may include any underlying device layer, electrode or separate substrate such as silicon wafer or polymer substrate for example.

In a particular embodiment of the present invention, the binder may be alignable, for example capable of forming a liquid crystalline phase. In that case the binder may assist alignment of the compound of formula I, for example such that their aromatic core is preferentially aligned along the direction of charge transport. Suitable processes for aligning the binder include those processes used to align polymeric organic semiconductors and are described in prior art, for example in US 2004/0248338 A1.

The formulation according to the present invention can additionally comprise one or more further components like for example surface-active compounds, lubricating agents, wetting agents, dispersing agents, hydrophobing agents, adhesive agents, flow improvers, defoaming agents, deaerators, diluents, reactive or non-reactive diluents, auxiliaries, colourants, dyes or pigments, furthermore, especially in case crosslinkable binders are used, catalysts, sensitizers, stabilizers, inhibitors, chain-transfer agents or co-reacting monomers.

The present invention also provides the use of the semiconducting compound, formulation or layer in an electronic device. The formulation may be used as a high mobility semiconducting material in various devices and apparatus. The formulation may be used, for example, in the form of a semiconducting layer or film. Accordingly, in another aspect, the present invention provides a semiconducting layer for use in an electronic device, the layer comprising the formulation according to the invention. The layer or film may be less than about 30 microns. For various electronic device applications, the thickness may be less than about 1 micron thick. The layer may be deposited, for example on a part of an electronic device, by any of the aforementioned solution coating or printing techniques.

The compounds and formulations according to the present invention are useful as charge transport, semiconducting, electrically conducting, photoconducting or light emitting materials in optical, electrooptical, electronic, electroluminescent or photoluminescent components or devices. Especially preferred devices are OFETs, TFTs, ICs, logic circuits, capacitors, RFID tags, OLEDs, OLETs, OPEDs, OPVs, solar cells, laser diodes, photoconductors, photodetectors, electrophotographic devices, electrophotographic recording devices, organic memory devices, sensor devices, charge injection layers, Schottky diodes, planarising layers, antistatic films, conducting substrates and conducting patterns. In these devices, the compounds of the present invention are typically applied as thin layers or films.

For example, the compound or formulation may be used as a layer or film, in a field effect transistor (FET) for example as the semiconducting channel, organic light emitting diode (OLED) for example as a hole or electron injection or transport layer or electroluminescent layer, photodetector, chemical detector, photovoltaic cell (PVs), capacitor sensor, logic circuit, display, memory device and the like. The compound or formulation may also be used in electrophotographic (EP) apparatus.

The compound or formulation is preferably solution coated to form a layer or film in the aforementioned devices or apparatus to provide advantages in cost and versatility of manufacture. The improved charge carrier mobility of the compound or formulation of the present invention enables such devices or apparatus to operate faster and/or more efficiently.

Especially preferred electronic device are OFETs, OLEDs and OPV devices, in particular bulk heterojunction (BHJ) OPV devices. In an OFET, for example, the active semiconductor channel between the drain and source may comprise the layer of the invention. As another example, in an OLED device, the charge (hole or electron) injection or transport layer or an emitting layer may comprise the layer of the invention.

For use in OPV devices the polymer according to the present invention is preferably used in a formulation that comprises or contains, more preferably consists essentially of, very preferably exclusively of, a p-type (electron donor) semiconductor and an n-type (electron acceptor) semiconductor. The p-type semiconductor is constituted by a compound according to the present invention. The n-type semiconductor can be an inorganic material such as zinc oxide or cadmium selenide, or an organic material such as a fullerene derivate, for example (6,6)-phenyl-butyric acid methyl ester derivatized methano $C_{60}$ fullerene, also known as "PCBM" or "$C_{60}$PCBM", as disclosed for example in G. Yu, J. Gao, J. C. Hummelen, F. Wudl, A. J. Heeger, Science 1995, 270, 1789 ff and having the structure shown below, or an structural analogous compound with e.g. a $C_{70}$ fullerene group ($C_{70}$PCBM), or a polymer (see for example Coakley, K. M. and McGehee, M. D. Chem. Mater. 2004, 16, 4533).

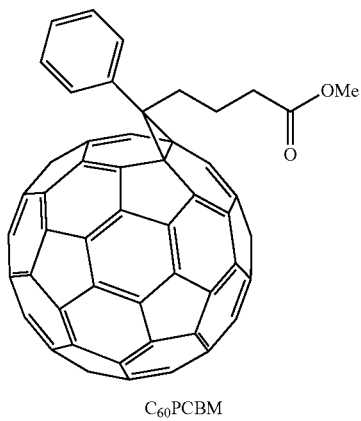 [SMILES: COC(=O)CCCC1(c2ccccc2)C23C=C4Cc5cc6cc7c8c9c(cc%10cc%11c%12c(c%13c%14c%15c(c4c5c4c6c8c(c%154)c4c9c%10c%12c%144)C%1321)C(=C3)C%11)C7]

$C_{60}$PCBM

A preferred material of this type is a blend or mixture of an acene compound according to the present invention with a $C_{60}$ or $C_{70}$ fullerene or modified fullerene like PCBM. Preferably the ratio acene:fullerene is from 2:1 to 1:2 by weight, more preferably from 1.2:1 to 1:1.2 by weight, most preferably 1:1 by weight. For the blended mixture, an optional annealing step may be necessary to optimize blend morphology and consequently OPV device performance.

The OPV device can for example be of any type known from the literature [see e.g. Waldauf et al., Appl. Phys. Lett., 2006, 89, 233517].

A first preferred OPV device according to the invention comprises:
 a low work function electrode (for example a metal, such as aluminum), and a high work function electrode (for example ITO), one of which is transparent,
 a layer (also referred to as "active layer") comprising a hole transporting material and an electron transporting material, preferably selected from OSC materials, situated between the electrodes; the active layer can exist for example as a bilayer or two distinct layers or blend or mixture of p-type and n-type semiconductor, forming a bulk heterjunction (BHJ) (see for example Coakley, K. M. and McGehee, M. D. Chem. Mater. 2004, 16, 4533),
 an optional conducting polymer layer, for example comprising a blend of PEDOT:PSS (poly(3,4-ethylenedioxythiophene):poly(styrenesulfonate)), situated between the active layer and the high work function electrode, to modify the work function of the high work function electrode to provide an ohmic contact for holes,
 an optional coating (for example of LiF) on the side of the low workfunction electrode facing the active layer, to provide an ohmic contact for electrons.

A second preferred OPV device according to the invention is an inverted OPV device and comprises:
 a low work function electrode (for example a metal, such as gold), and a high work function electrode (for example ITO), one of which is transparent,
 a layer (also referred to as "active layer") comprising a hole transporting material and an electron transporting material, preferably selected from OSC materials, situated between the electrodes; the active layer can exist for example as a bilayer or two distinct layers or blend or mixture of p-type and n-type semiconductor, forming a BHJ,
 an optional conducting polymer layer, for example comprising a blend of PEDOT:PSS, situated between the active layer and the low work function electrode to provide an ohmic contact for electrons,
 an optional coating (for example of $TiO_x$) on the side of the high workfunction electrode facing the active layer, to provide an ohmic contact for holes.

In the OPV devices of the present invent invention the p-type and n-type semiconductor materials are preferably selected from the materials, like the p-type compound/fullerene systems, as described above. If the bilayer is a blend an optional annealing step may be necessary to optimize device performance.

The compound, formulation and layer of the present invention are also suitable for use in an OFET as the semiconducting channel. Accordingly, the invention also provides an OFET comprising a gate electrode, an insulating (or gate insulator) layer, a source electrode, a drain electrode and an organic semiconducting channel connecting the source and drain electrodes, wherein the organic semiconducting channel comprises a compound, formulation or organic semiconducting layer according to the present invention. Other features of the OFET are well known to those skilled in the art.

OFETs where an OSC material is arranged as a thin film between a gate dielectric and a drain and a source electrode, are generally known, and are described for example in U.S. Pat. No. 5,892,244, U.S. Pat. No. 5,998,804, U.S. Pat. No. 6,723,394 and in the references cited in the background section. Due to the advantages, like low cost production using the solubility properties of the compounds according to the invention and thus the processibility of large surfaces, preferred applications of these FETs are such as integrated circuitry, TFT displays and security applications.

The gate, source and drain electrodes and the insulating and semiconducting layer in the OFET device may be arranged in any sequence, provided that the source and drain electrode are separated from the gate electrode by the insulating layer, the gate electrode and the semiconductor layer both contact the insulating layer, and the source electrode and the drain electrode both contact the semiconducting layer.

An OFET device according to the present invention preferably comprises:
 a source electrode,
 a drain electrode,
 a gate electrode,
 a semiconducting layer,
 one or more gate insulator layers,
 optionally a substrate.

wherein the semiconductor layer preferably comprises a compound or formulation as described above and below.

The OFET device can be a top gate device or a bottom gate device.

Suitable structures and manufacturing methods of an OFET device are known to the skilled in the art and are described in the literature, for example in US 2007/0102696 A1.

The gate insulator layer preferably comprises a fluoropolymer, like e.g. the commercially available Cytop 809M® or Cytop 107M® (from Asahi Glass).

Preferably the gate insulator layer is deposited, e.g. by spin-coating, doctor blading, wire bar coating, spray or dip coating or other known methods, from a formulation comprising an insulator material and one or more solvents with one or more fluoro atoms (fluorosolvents), preferably a perfluorosolvent. A suitable perfluorosolvent is e.g. FC75® (available from Acros, catalogue number 12380). Other suitable fluoropolymers and fluorosolvents are known in prior art, like for example the perfluoro-polymers Teflon AFC® 1600 or 2400 (from DuPont) or Fluoropel® (from Cytonix) or the perfluorosolvent FC 43® (Acros, No. 12377). Especially preferred are organic dielectric materials having a low permittivity (or dielectric contant) from 1.0 to 5.0, very preferably from 1.8 to 4.0 ("low k materials"), as disclosed for example in US 2007/0102696 A1 or U.S. Pat. No. 7,095,044.

In security applications, OFETs and other devices with semiconducting materials according to the present invention, like transistors or diodes, can be used for RFID tags or security markings to authenticate and prevent counterfeiting of documents of value like banknotes, credit cards or ID cards, national ID documents, licenses or any product with monetry value, like stamps, tickets, shares, cheques etc.

Alternatively, the materials according to the invention can be used in OLEDs, e.g. as the active display material in a flat panel display applications, or as backlight of a flat panel display like e.g. a liquid crystal display. Common OLEDs are realized using multilayer structures. An emission layer is generally sandwiched between one or more electron-transport and/or hole-transport layers. By applying an electric voltage electrons and holes as charge carriers move towards the emission layer where their recombination leads to the excitation and hence luminescence of the lumophor units contained in the emission layer. The inventive compounds, materials and films may be employed in one or more of the charge transport layers and/or in the emission layer, corresponding to their electrical and/or optical properties. Furthermore their use within the emission layer is especially advantageous, if the compounds, materials and films according to the invention show electroluminescent properties themselves or comprise electroluminescent groups or compounds. The selection, characterization as well as the processing of suitable monomeric, oligomeric and polymeric compounds or materials for the use in OLEDs is generally known by a person skilled in the art, see, e.g., Müller, *Synth. Metals,* 2000, 111-112, 31, Alcala, *J. Appl. Phys.,* 2000, 88, 7124 and the literature cited therein.

According to another use, the materials according to this invention, especially those showing photoluminescent properties, may be employed as materials of light sources, e.g. in display devices, as described in EP 0889350 A1 or by C. Weder et al., *Science,* 1998, 279, 835.

A further aspect of the invention relates to both the oxidised and reduced form of the compounds according to this invention. Either loss or gain of electrons results in formation of a highly delocalised ionic form, which is of high conductivity. This can occur on exposure to common dopants. Suitable dopants and methods of doping are known to those skilled in the art, e.g. from EP 0 528 662, U.S. Pat. No. 5,198,153 or WO 96/21659.

The doping process typically implies treatment of the semiconductor material with an oxidating or reducing agent in a redox reaction to form delocalised ionic centres in the material, with the corresponding counterions derived from the applied dopants. Suitable doping methods comprise for example exposure to a doping vapor in the atmospheric pressure or at a reduced pressure, electrochemical doping in a solution containing a dopant, bringing a dopant into contact with the semiconductor material to be thermally diffused, and ion-implantantion of the dopant into the semiconductor material.

When electrons are used as carriers, suitable dopants are for example halogens (e.g., $I_2$, $Cl_2$, $Br_2$, ICl, $ICl_3$, IBr and IF), Lewis acids (e.g., $PF_5$, $AsF_5$, $SbF_5$, $BF_3$, $BCl_3$, $SbCl_5$, $BBr_3$ and $SO_3$), protonic acids, organic acids, or amino acids (e.g., HF, HCl, $HNO_3$, $H_2SO_4$, $HClO_4$, $FSO_3H$ and $ClSO_3H$), transition metal compounds (e.g., $FeCl_3$, FeOCl, $Fe(ClO_4)_3$, $Fe(4-CH_3C_6H_4SO_3)_3$, $TiCl_4$, $ZrCl_4$, $HfCl_4$, $NbF_5$, $NbCl_5$, $TaCl_5$, $MoF_5$, $MoCl_5$, $WF_5$, $WCl_6$, $UF_6$ and $LnCl_3$ (wherein Ln is a lanthanoid), anions (e.g., $Cl^-$, $Br^-$, $I^-$, $I_3^-$, $HSO_4^-$, $SO_4^{2-}$, $NO_3^-$, $ClO_4^-$, $BF_4^-$, $PF_6^-$, $AsF_6^-$, $SbF_6^-$, $FeCl_4^-$, $Fe(CN)_6^{3-}$, and anions of various sulfonic acids, such as aryl-$SO_3^-$). When holes are used as carriers, examples of dopants are cations (e.g., $H^+$, $Li^+$, $Na^+$, $K^+$, $Rb^+$ and $Cs^+$), alkali metals (e.g., Li, Na, K, Rb, and Cs), alkaline-earth metals (e.g., Ca, Sr, and Ba), $O_2$, $XeOF_4$, $(NO_2^+)$ $(SbF_6^-)$, $(NO_2^+)$ $(SbCl_6^-)$, $(NO_2^+)$ $(BF_4^-)$, $AgClO_4$, $H_2IrCl_6$, La$(NO_3)_3.6H_2O$, $FSO_2OOSO_2F$, Eu, acetylcholine, $R_4N^+$, (R is an alkyl group), $R_4P^+$ (R is an alkyl group), $R_6As^+$ (R is an alkyl group), and $R_3S^+$ (R is an alkyl group).

The conducting form of the compounds of the present invention can be used as an organic "metal" in applications including, but not limited to, charge injection layers and ITO planarising layers in OLED applications, films for flat panel displays and touch screens, antistatic films, printed conductive substrates, patterns or tracts in electronic applications such as printed circuit boards and condensers.

The compounds and formulations according to the present invention may also be suitable for use in organic plasmon-emitting diodes (OPEDs), as described for example in Koller et al., *Nat. Photonics,* 2008, 2, 684.

According to another use, the materials according to the present invention can be used alone or together with other materials in or as alignment layers in LCD or OLED devices, as described for example in US 2003/0021913. The use of charge transport compounds according to the present invention can increase the electrical conductivity of the alignment layer. When used in an LCD, this increased electrical conductivity can reduce adverse residual dc effects in the switchable LCD cell and suppress image sticking or, for example in ferroelectric LCDs, reduce the residual charge produced by the switching of the spontaneous polarisation charge of the ferroelectric LCs. When used in an OLED device comprising a light emitting material provided onto the alignment layer, this increased electrical conductivity can enhance the electroluminescence of the light emitting material. The compounds or materials according to the present invention having mesogenic or liquid crystalline properties can form oriented anisotropic films as described above, which are especially useful as alignment layers to induce or enhance alignment in a liquid crystal medium provided onto said anisotropic film. The materials according to the present invention may also be combined with photoisomerisable compounds and/or chromophores for use in or as photoalignment layers, as described in US 2003/0021913.

According to another use, the materials according to the present invention, especially their water-soluble derivatives (for example with polar or ionic side groups) or ionically doped forms, can be employed as chemical sensors or materials for detecting and discriminating DNA sequences. Such uses are described for example in L. Chen, D. W. McBranch, H. Wang, R. Helgeson, F. Wudl and D. G. Whitten, *Proc. Natl. Acad. Sci. U.S.A.* 1999, 96, 12287; D. Wang, X. Gong, P. S. Heeger, F. Rininsland, G. C. Bazan and A. J. Heeger, *Proc. Natl. Acad. Sci. U.S.A.* 2002, 99, 49; N. DiCesare, M. R. Pinot, K. S. Schanze and J. R. Lakowicz, *Langmuir* 2002, 18, 7785; D. T. McQuade, A. E. Pullen, T. M. Swager, *Chem. Rev.* 2000, 100, 2537.

Unless the context clearly indicates otherwise, as used herein plural forms of the terms herein are to be construed as including the singular form and vice versa.

Throughout the description and claims of this specification, the words "comprise" and "contain" and variations of the words, for example "comprising" and "comprises", mean "including but not limited to", and are not intended to (and do not) exclude other components.

It will be appreciated that variations to the foregoing embodiments of the invention can be made while still falling within the scope of the invention. Each feature disclosed in this specification, unless stated otherwise, may be replaced by alternative features serving the same, equivalent or similar purpose. Thus, unless stated otherwise, each feature disclosed is one example only of a generic series of equivalent or similar features.

All of the features disclosed in this specification may be combined in any combination, except combinations where at least some of such features and/or steps are mutually exclusive. In particular, the preferred features of the invention are applicable to all aspects of the invention and may be used in any combination. Likewise, features described in non-essential combinations may be used separately (not in combination).

It will be appreciated that many of the features described above, particularly of the preferred embodiments, are inventive in their own right and not just as part of an embodiment of the present invention. Independent protection may be sought for these features in addition to or alternative to any invention presently claimed.

The invention will now be described in more detail by reference to the following examples, which are illustrative only and do not limit the scope of the invention.

Unless stated otherwise, above and below percentages are percent by weight and temperatures are given in degrees Celsius.

EXAMPLES

Example 1

Compound (1) is prepared as described below:

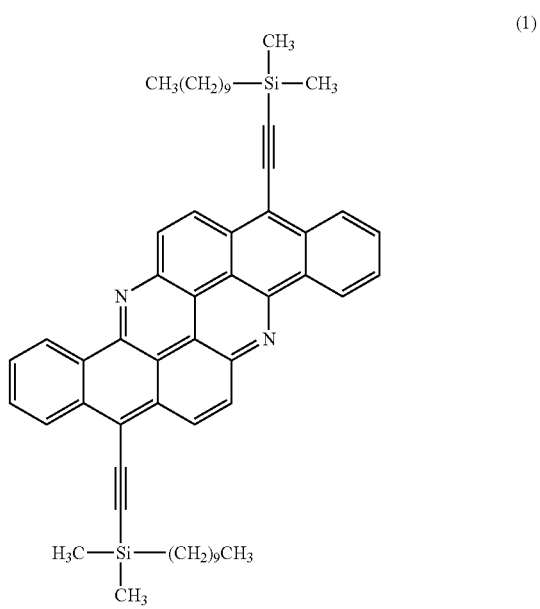

Precursor 1: Decyldimethylethynylsilane

A round bottom flask was charged with chlorodecyldimethylsilane (12.362 g; 50.00 mmol) and the flask was cooled with an ice-water bath to 0° C. Ethynylmagnesium bromide (0.5M in THF, 125.0 cm$^3$, 62.50 mmol) was added into the flask over 30 min. The cooling bath was removed and the mixture was stirred at 50° C. for an additional hour.

The mixture was concentrated by vacuum evaporation to dryness. Petroleum ether 40-60 (50 cm$^3$) was added and the mixture was suction filtered through a silica plug (washed with petroleum ether 40-60) to yield a colourless solution. The solvent was removed by vacuum evaporation again and the residue was vacuum distilled (200° C. at 8 mbar) on a Kugelrohr apparatus to yield a colourless liquid (10.10 g, 89%). GCMS (m/z): [209, M-15] 99.2%. $^1$HNMR (300 MHz, CDCl$_3$,): δ=0.17 (s, 6H), 0.63 (m, 2H), 0.88 (t, 6.0 Hz, 3H), 1.2-1.4 (m, 16H), 2.37 (s, 1H).

Compound 1:
8,16-Bis(decyldimethylsilylethynyl)flavanthrene

To a solution of decylethynyldimethylsilane (1.851 g, 8.00 mmol) in anhydrous THF (30 cm$^3$) was added at 0° C. n-butyllithium (2.5M in hexanes, 3.2 cm$^3$; 8.00 mmol) dropwise within 5 minutes to yield a colourless clear solution. The cooling bath was removed and the solution was stirred at 22° C. for an additional 30 minutes. The reaction mixture remained as a clear colourless solution. Flavanthrone (0.817 g, 2.00 mmol) was added in one portion as a solid (deep yellow) and the mixture was supersonicated for ca. 2 minutes, then stirred at 22° C. for 2 hours. The mixture was then placed in an oil-bath and stirred at 55° C. for 20 hours to yield a pale-brown suspension.

The reaction was quenched with saturated ammonium chloride solution (50 cm$^3$) and the 2-layer mixture was stirred at 22° C. for 30 minutes. The upper organic layer was separated and the aqueous later was extracted with diethyl ether (2×20 cm$^3$). The solvents of the combined organic extracts were removed by vacuum evaporation and the brown residue was dissolved in chloroform, then suction filtered through a silica plug (washed with chloroform). The filtrate (brown-red solution) was vacuum evaporated to dryness to yield a brown-red oily residue which was purified by flash-column chromatography on silica (eluent: DCM) to yield a brown-red solid. The solid was subjected to another flash-column purification on silica (eluent: 1:1 chloroform-cyclohexane) to yield a dark red micro crystalline solid (0.245 g, 15%). $^1$HNMR (CDCl$_3$, 300 MHz): δ=0.54 (s, 6H), 0.87 (t, 6 Hz, 3H), 1.00 (m, 2H), 1.2-1.5 (m, 12H), 1.57 (m, 2H), 1.73 (m, 2H), 7.90 (m, 2H), 8.26 (d, 9 Hz, 1H), 8.75 (m, 2H), 9.72 (d, 9 Hz, 1H). MS (ES+): m/z 823.7.

Example 2

Compound (2) is prepared as described below:

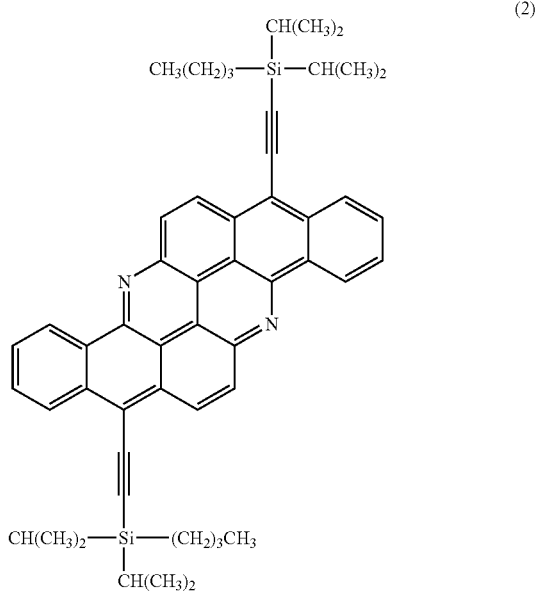

(2)

Precursor 2:
Butyl-diisopropyl(trimethylsilanylethynyl)silane

To the solution of dichlorodiisopropylsilane (9.545 g; 50.00 mmol) in anhydrous THF (25.0 cm$^3$) was added n-butyllithium solution (2.5 M, 20.4 cm$^3$; 51.00 mmol), over 30 min, at −78° C., to yield a white suspension. The suspension was stirred at the low temperature for an additional 1 h before the cooling bath was removed and stirred at 22° C. for 1 h. The mixture remained as a white suspension.

Lithium trimethylsilylacetylide solution (1.5 M in THF, 36.7 cm$^3$; 55.00 mmol) was added through syringe at 22° C. quickly. The mixture was kept stirred at 22° C. for an additional hour (remained as white suspension). The white solid of suspension was removed by suction filteration. The filtrated was vacuum evaporated and the pale-yellow oil residue was filtered through a silica plug (0.5 cm, washed with diethyl ether). The filtrate was vacuum evaporated and the residual oil was vacuum distilled on a Kugelrohr apparatus at 150° C., 6 mbar, to yield a colourless liquid (12.60 g, 94%). $^1$HNMR (CDCl$_3$, 300 MHz): δ=0.17 (s, 9H), 0.60 (m, 2H), 0.90 (t, 7.5 Hz, 3H), 1.03 (m, 14H), 1.36 (m, 4H); $^{13}$CNMR (CDCl$_3$, 75 MHz): δ=0.02, 9.7, 11.6, 13.8, 18.0, 18.2, 26.6, 26.7, 110.5, 115.9.

Precursor 3: Butylethynyldiisopropylsilane

To the solution of precursor 2 (15.000 g; 49.15 mmol) in dichloromethane (30 cm$^3$) and methanol (30 cm$^3$) was added grounded K$_2$CO$_3$ (13.019 g; 94.20 mmol) in one portion. The mixture was stirred at 22° C. for 2 h. The solid was suction filtered off through a silica pad. The filtrate was vacuum evaporated to dryness to yield a colourless liquid. The liquid was vacuum fractionated at 20 mbar and the product was collected between 95-99° C. as colourless liquid (7.69 g, 59%). $^1$HNMR (CDCl$_3$, 300 MHz): δ=0.47 (m, 2H), 0.73 (t, 7.5 Hz, 3H), 0.89 (m, 14H), 1.20 (m, 4H), 2.18 (s, 1H).

Compound 2:
8,16-Bis(butyldiisopropylsilylethynyl)flavanthrene

To the solution of butylethynyldiisopropylsilane (1.654 g; 8.00 mmol) in 1,4-dioxane (anhydrous, 30 cm$^3$) was added at 0° C. n-butyllithium (3.2 cm$^3$; 8.00 mmol) dropwise within 5 min to yield a milky white solution. The cooling bath was removed and the solution was stirred at 22° C. for an additional 30 min.

Flavanthrone (0.817 g; 2.00 mmol) was added in one portion and the mixture was supersonicated for ca. 2 min then stirred at 22° C. for 4.5 h. The yellow mixture was placed in an oil-bath and stirred at 50° C. for an additional 60 h to yield a red suspension.

The reaction mixture was cooled to RT then quenched with saturated NH$_4$Cl solution (50 cm$^3$) to yield a yellow slurry floated on top of the clear aqueous solution. The slurry was taken into THF (3×30 cm$^3$) and the THF suspension was vacuum evaporated to dryness. Methanol (100 cm$^3$) was added to the residue and mixture was suction filtered to yield an orange-yellow powdery solid.

The solid was mixed with acetic acid (40 cm$^3$), KI (1.660 g; 10.00 mmol), sodium hypophosphite (0.880 g; 10.00 mmol) and the mixture was stirred at 120° C. (external) for 2 h, to yield a brown-red suspension. The suspension was cooled to 22° C. followed by the addition of methanol (50 cm$^3$). The reddish brown solid was suction filtered off, washed with methanol and air dried. The solid was flash-columned on silica eluted with 3:2 cyclohexane-chloroform to yield a brown-red micro crystalline solid (1.39 g, 90.3%). M.p.: 339° C. (DSC). $^1$HNMR (CDCl$_3$, 300 MHz): δ=1.02 (m, 2H), 1.10 (t, 7.5 Hz, 3H), 1.40 (m, 14H), 1.61 (m, 2H), 1.77 (m, 2H), 7.57 (t, 7.5 Hz, 1H), 7.71 (t, 7.5 Hz, 1H), 8.11 (d, 9 Hz, 1H), 8.49 (d, 9 Hz, 1H), 8.68 (d, 9 Hz, 1H), 9.38 (d, 9 Hz, 1H).

Example 3

Compound (3) is prepared as described below:

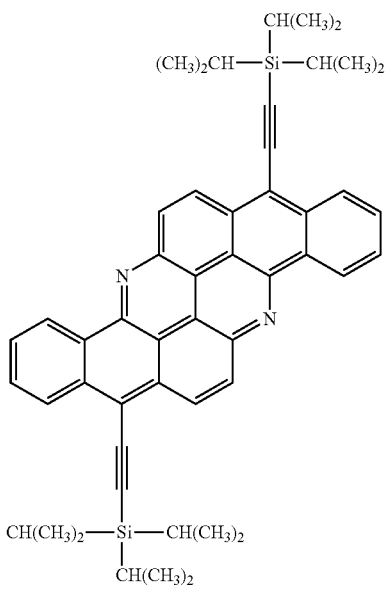

Compound 3:
8,16-Bis(triisopropylsilylethynyl)flavanthrene

To the solution of ethynyltriisopropylsilane (1.536 g; 8.00 mmol) in 1,4-dioxane anhydrous (30 cm³) was added at 0° C. n-BuLi (2.5M in hexanes, 3.2 cm³; 8.00 mmol) dropwise over 5 min to yield a white suspension. The cooling bath was removed and the suspension was stirred at 22° C. for an additional 30 min. Flavanthrone (0.817 g; 2.00 mmol) was added in one portion and the mixture was supersonicated for ca. 2 min then stirred at 22° C. for 55 h to yield an orange yellow milky solution. The yellow mixture was placed in an oil-bath and stirred at 50° C. for an additional 4 h. The reaction mixture was cooled to RT then quenched with saturated NH₄Cl solution (50 cm³) to yield a yellow slurry floated on top of the clear aqueous solution. The slurry was taken into THF (100 cm³) to yield a yellow suspension, which was washed once with brine. The THF suspension was rota evaporated to dryness. Methanol (100 cm³) was added to the residue and mixture was suction filtered to yield a yellow solid.

The solid was mixed with acetic acid (40 cm³), potassium iodide (1.660 g; 10.00 mmol), sodium hypophosphite (0.880 g; 10.00 mmol; 500) and the mixture was stirred at 120° C. (external) for 1 h, to yield a purple-brown suspension. The suspension was cooled to RT followed by the addition of methanol (50 cm³). The precipitate was suction filtered off, washed with methanol, air-dried then flash chromatographed on silica (eluent 3:2 v/v cyclohexane-chloroform, Rf=0.5) to yield a coffee coloured solid. The solid was recrystallised from chloroform-ethanol to afford brown-red hairy needles (1.16 g, 78%). M.P.: 387° C. (DSC). ¹HNMR (CDCl₃, 300 MHz): δ=1.45 (m, 21H), 7.49 (t, 7.5 Hz, 1H), 7.64 (t, 7.5 Hz, 1H), 8.11 (d, 9.0 Hz, 1H), 8.47 (d, 9.0 Hz, 1H), 8.68 (d, 9.0 Hz, 1H), 9.33 (d, 9.0 Hz, 1H).

Example 4

Transistor Fabrication and Measurement

Top-gate thin-film organic field-effect transistors (OFETs) were fabricated on glass substrates with thermally evaporated Au source-drain electrodes. A 0.5 wt. % solution of each compound (solvent see Table 1) was spin-coated on the top. The film was annealed at 100° C. for 30 seconds. Next a fluoropolymer dielectric material (D139) was spin-coated. Finally a Au gate electrode was deposited by thermal evaporation. The electrical characterization of the transistor devices was carried out in ambient air atmosphere using computer controlled Agilent 4155C Semiconductor Parameter Analyser. Charge carrier mobility in the saturation regime ($\mu_{sat}$) was calculated for the compound and the results are summarized in Table 1. Field-effect mobility was calculated in the saturation regime ($V_d > (V_g - V_0)$) using equation (1):

$$\left(\frac{dI_d^{sat}}{dV_g}\right)_{V_d} = \frac{WC_i}{L}\mu^{sat}(V_g - V_0) \quad (1)$$

where W is the channel width, L the channel length, $C_i$ the capacitance of insulating layer, $V_g$ the gate voltage, $V_0$ the turn-on voltage, and $\mu_{sat}$ is the charge carrier mobility in the saturation regime. Turn-on voltage ($V_0$) was determined as the onset of source-drain current.

TABLE 1

Mobilties ($\mu_{sat}$) for compounds (1)-(2) in top-gate OFETs.

| Compound | Solvent | Mobility ($\mu_{sat}$)/cm²/Vs |
|---|---|---|
| (1) | mesitylene | 0.052 |
| (2) | cyclohexanone | 0.013 |

The invention claimed is:
1. A compound of formula I

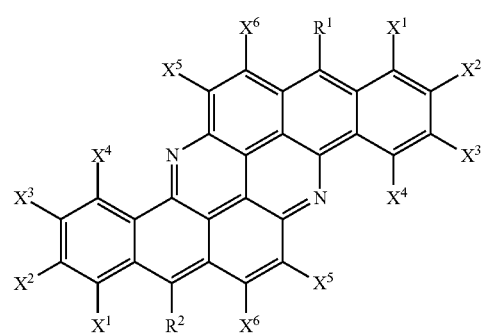

wherein the individual groups have the following meanings

R¹ and R² independently of each other denote —C≡C—R³,

R3 is an optionally substituted alkyl, silyl or germyl group, or an aryl or heteroaryl group with 1 to 20 ring atoms which is unsubstituted or substituted by one or more groups L X¹ to X⁶ independently of each other, and on each occurrence identically or differently, denote H or have one of the meanings given for L, L is selected from P-Sp-, F, Cl, Br, I, —OH, —CN, —NO₂, —NCO, —NCS, —OCN, —SCN, —C(=O)NR⁰R⁰⁰, —C(=O)X⁰, —C(=O)R⁰, —NR⁰R⁰⁰, C(=O)OH, optionally substituted silyl or germyl, optionally substituted aryl or heteroaryl having 4 to 20 ring atoms, straight chain, branched or cyclic alkyl, which is optionally substituted, alkoxy, oxaalkyl or thioalkyl with 1 to 20, preferably 1 to 12 C atoms which is unsubstituted or substituted with one or more F or Cl atoms or OH groups, and straight chain, branched or cyclic alkenyl, alkynyl, alkylcarbonyl, alkoxycarbonyl, alkylcarbonyloxy or alkoxycarbonyloxy with 2 to 30, preferably 2 to 12 C atoms which is unsubstituted or substituted with one or more F or Cl atoms or OH groups, P is a polymerisable group, Sp is a spacer group or a single bond, X⁰ is halogen, R⁰, R⁰⁰ independently of each other denote H or alkyl with 1 to 20 C-atoms, Y⁰, Y⁰⁰ independently of each other denote H, F, Cl or CN.

2. The compound according to claim 1, wherein R³ is a group of formula II

-AR'R''R'''      II wherein

A is C, Si or Ge, preferably Si,

R', R'', R''' are identical or different groups selected from the group consisting of H, a straight-chain, branched or cyclic alkyl or alkoxy group having 1 to 20 C atoms, a straight-chain, branched or cyclic alkenyl group having 2 to 20 C atoms, a straight-chain, branched or cyclic alkynyl group having 2 to 20 C atoms, a straight-chain, branched or cyclic alkylcarbonyl group having 2 to 20 C atoms, an aryl or heteroaryl group having 4 to 20 ring atoms, an arylalkyl or heteroarylalkyl group having 4 to 20 ring atoms, an aryloxy or heteroaryloxy group having 4 to 20 ring atoms, or an arylalkyloxy or heteroarylalkyloxy group having 4 to 20 ring atoms, wherein all the aforementioned groups are optionally substituted with one or more groups L', and L' has one of the meanings given for L in formula I, which is different from a silyl and germyl group.

3. The compound according to claim 1, wherein X¹, X², X³, X⁴, X⁵ and X⁶ are H.

4. The compound according to claim 1, wherein X¹, X², X³, X⁴, X⁵ and X⁶ are selected from the group consisting of H, F, Cl, Br, I, —CN, and straight chain, branched or cyclic alkyl, alkoxy, thioalkyl, alkenyl, alkynyl, alkylcarbonyl, alkoxycarbonyl, alkylcarbonyloxy, alkylcarbonylamido, alkylamidocarbonyl or alkoxycarbonyloxy with 1 to 20, preferably 1 to 12 C atoms which is unsubstituted or substituted with one or more F or Cl atoms or OH groups or perfluorinated, and aromatic and heteroaromatic groups with 4 to 25 ring atoms, which are mono- or polycyclic, i.e. which may also contain two or more individual rings that are connected to each other via single bonds, or contain two or more fused rings, and wherein each ring is unsubstituted or substituted with one or more groups L as defined in claim 1.

5. The compound according to claim 1,

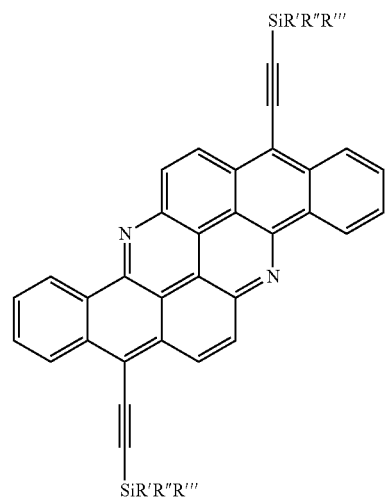

wherein R', R'' and R''' are identical or different groups selected from the group consisting of H, a straight-chain, branched or cyclic alkyl or alkoxy group having 1 to 20 C atoms, a straight-chain, branched or cyclic alkenyl group having 2 to 20 C atoms, a straight-chain, branched or cyclic alkynyl group having 2 to 20 C atoms, a straight-chain, branched or cyclic alkylcarbonyl group having 2 to 20 C atoms, an aryl or heteroaryl group having 4 to 20 ring atoms, an arylalkyl or heteroarylalkyl group having 4 to 20 ring atoms, an aryloxy or heteroaryloxy group having 4 to 20 ring atoms, or an arylalkyloxy or heteroarylalkyloxy group having 4 to 20 ring atoms, wherein all the aforementioned groups are optionally substituted with one or more groups L', and L' has one of the meanings given for L in formula I, which is different from a silyl and germyl group.

6. A formulation comprising one or more compounds according to claim 1 and one or more organic solvents.

7. A formulation comprising one or more compounds according to claim 1, one or more organic binders or precursors thereof, preferably having a permittivity ∈ at 1,000 Hz of 3.3 or less, and optionally one or more solvents.

8. A method of using compounds according to claim 1 as a charge transport, semiconducting, electrically conducting, photoconducting or light emitting material, which comprises incorporating a compound of claim 1 into an optical, electrooptical, electronic, electroluminescent or photoluminescent components or devices.

9. A charge transport, semiconducting, electrically conducting, photoconducting or light emitting material or component comprising one or more compounds or formulations according to claim 1.

10. An optical, electrooptical, electronic, electroluminescent or photoluminescent component or device comprising one or more compounds, formulations, materials or components according to claim 1.

11. A component or device according to claim 10, wherein said component is an organic field effect transistor (OFET), a thin film transistor (TFT), an integrated circuit (IC), a logic circuit, a capacitor, a radio frequency identification (RFID) tag, a device or component, an organic light emitting diode (OLED), an organic light emitting transistor (OLET), a flat panel display, a backlight of a display, an organic photovoltaic device (OPV), a solar cell, a laser diode, a photoconductor, a photodetector, a electrophotographic device, a electrophotographic recording device, an organic memory device, a sensor device, a charge injection layer, a charge transport layer or an interlayer in a polymer light emitting diode (PLEDs), an organic plasmon-emitting diode (OPEDs), a Schottky diode, a planarising layer, an antistatic film, a polymer electrolyte membrane (PEM), a conducting substrate, a conducting pattern, an electrode material in a battery, an alignment layer, a biosensor, a biochip, a security marking, a security device or a component or device for detecting and discriminating a DNA sequence.

* * * * *